United States Patent [19]

Ueda et al.

[11] 4,377,580
[45] Mar. 22, 1983

[54] TRICYCLIC QUINAZOLINE DERIVATIVES

[75] Inventors: Ikuo Ueda, Toyonaka; Masayuki Kato, Minoo; Masanobu Nagano, Ikeda, all of Japan

[73] Assignee: Fujisawa Pharmaceutical Co., Ltd., Osaka, Japan

[21] Appl. No.: 210,340

[22] Filed: Nov. 25, 1980

[30] Foreign Application Priority Data

Dec. 3, 1979 [GB] United Kingdom ............... 7941607
Oct. 3, 1980 [GB] United Kingdom ............... 8031965

[51] Int. Cl.³ ............... A61K 31/505; C07D 487/04; C07D 239/80; C07D 471/14
[52] U.S. Cl. ............... 424/251; 544/245; 544/247; 544/250; 544/286; 544/291; 544/293
[58] Field of Search ............... 544/250; 424/251

[56] References Cited

U.S. PATENT DOCUMENTS

| | | | |
|---|---|---|---|
| 3,594,379 | 7/1971 | Hardtmann et al. | 424/251 |
| 3,891,638 | 6/1975 | Inaba et al. | 544/250 |
| 4,105,766 | 8/1978 | Alexander | 544/250 |
| 4,167,569 | 9/1979 | Mills | 544/250 |
| 4,192,944 | 3/1980 | Juby | 544/250 |

FOREIGN PATENT DOCUMENTS 1086666 10/1967 United Kingdom ............... 544/250
1349136 3/1974 United Kingdom .

OTHER PUBLICATIONS

Salvatore Plescia et al., Journal of Heterocyclic Chemistry vol. 11, pp. 603–606 (1974).

Primary Examiner—Donald G. Daus
Assistant Examiner—J. Turnipseed
Attorney, Agent, or Firm—Dayton R. Stemple

[57] ABSTRACT

Quinazoline derivatives of the formulae:

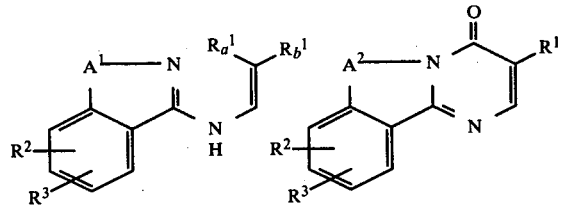

wherein
$A^1$ is

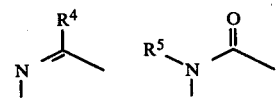

$A^2$ is

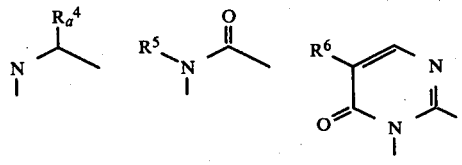

$R^1$ is hydrogen, carboxy or esterified carboxy,
$R_a^1$ and $R_b^1$ are esterified carboxy,
$R^2$ and $R^3$ are hydrogen, alkyl, halogen, nitro, amino, alkoxy, aryloxy, alkylthio, alkylpiperazinyl, acylamino or dialkylamino which may be substituted with hydroxy,
$R^4$ is hydrogen, alkyl, hydroxy, alkoxy, alkenyloxy, dialkylamino or 2,2-dialkoxycarbonylvinylamino
$R_a^4$ is hydrogen, alkyl, hydroxy, alkoxy, alkenyloxy or dialkylamino,
$R^5$ is alkyl or alkenyl, and
$R^6$ is carboxy or esterified carboxy.

10 Claims, No Drawings

TRICYCLIC QUINAZOLINE DERIVATIVES

This invention relates to new quinazoline derivatives. More particularly, it relates to new quinazoline derivatives, to processes for preparation thereof, to a pharmaceutical composition comprising the same, and to a method of use of the same in the treatment of symptoms associated with allergic manifestations, e.g. asthmatic conditions.

Accordingly, it is an object of this invention to provide new quinazoline derivatives which are useful as antiallergic agent.

Another object of this invention is to provide processes for preparing the quinazoline derivatives.

Further object of the invention is to provide a pharmaceutical composition comprising the quinazoline derivatives.

Quinazoline derivatives of this invention include quinazoline compounds of the formula:

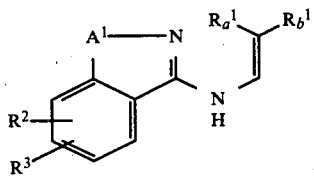

wherein
$R_a^1$ and $R_b^1$ are esterified carboxy,
$R^2$ and $R^3$ are hydrogen, alkyl, halogen, nitro, amino, alkoxy, aryloxy, alkylthio, alkylpiperazinyl, acylamino or dialkylamino which may be substituted with hydroxy,
$A^1$ is a group of the formula:

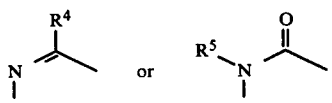

in which
$R^4$ is hydrogen, alkyl, hydroxy, alkoxy, alkenyloxy, dialkylamino or 2,2-dialkoxycarbonylvinylamino, and
$R^5$ is alkyl or alkenyl, and pyrimidoquinazoline compounds of the formula:

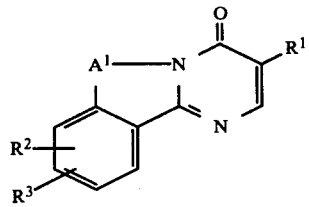

wherein
$R^1$ is hydrogen, carboxy or esterified carboxy,
$A^2$ is a group of the formula:

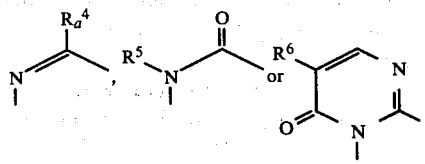

in which
$R_a^4$ is hydrogen, alkyl, hydroxy, alkoxy, alkenyloxy or dialkylamino,
$R^6$ is carboxy or esterified carboxy and
$R^5$ is the same as defined above, and
$R^2$ and $R^3$ are each as defined above.

Particulars of the above definitions and suitable examples thereof are explained as follows.

As to the term "lower" used in the specification and claims, it is to be understood that it means the one having 1 to 6 carbon atom(s), unless otherwise provided.

Suitable esterified carboxy for $R^1$, $R_a^1$, $R_b^1$ and $R^6$ may be lower alkoxycarbonyl having 2 to 7 carbon atom(s) (e.g. methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl) and the like. Further, the esterified carboxy of $R_a^1$ and $R_b^1$ may be linked together to form a group of the formula:

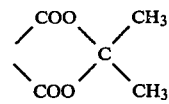

Suitable alkyl for $R^2$, $R^3$, $R^4$, $R_a^4$ and $R^5$ may be straight or branched lower alkyl (e.g. methyl, ethyl, propyl, isopropyl, butyl, isobutyl, t-butyl, pentyl, hexyl).

The halogen for $R^2$ and $R^3$ may be fluorine, chlorine, bromine and iodine.

Suitable alkoxy for $R^2$, $R^3$, $R^4$ and $R_a^4$ may be straight or branched lower alkoxy (e.g. methoxy, ethoxy, propoxy, isopropoxy, butoxy, isobutoxy, t-butoxy, pentyloxy, hexyloxy).

Suitable aryloxy for $R^2$ and $R^3$ may be phenoxy, naphthyloxy, tolyloxy or the like.

Suitable alkylthio for $R^2$ and $R^3$ may be straight or branched lower alkylthio (e.g. methylthio, ethylthio, propylthio, isopropylthio, butylthio, isobutylthio, t-butylthio, pentylthio, hexylthio).

Suitable dialkylamino for $R^2$, $R^3$, $R^4$ and $R_a^4$ may be di(lower)alkylamino (e.g. dimethylamino, diethylamino, dipropylamino, diisopropylamino, dibutylamino), and the alkyl moiety of said dialkylamino group may be substituted with hydroxy to form bis(hydroxyalkyl)amino (e.g. bis(hydroxyethyl)amino, etc.).

Suitable alkylpiperazinyl for $R^2$ and $R^3$ may be 4-lower alkyl piperazinyl (e.g. 4-methylpiperazinyl, 4-ethylpiperazinyl, 4-propylpiperazinyl, 4-isopropylpiperazinyl, 4-t-butylpiperazinyl, 4-pentylpiperazinyl, 4-hexylpiperazinyl).

The acylamino group for $R^2$ and $R^3$ includes both of monoacylamino group and diacylamino group. Acyl moiety of the acylamino group may include the residue of organic carboxylic acid and organic sulfonic acid. Suitable acyl may be alkanoyl including lower alkanoyl (e.g. formyl, acetyl, propionyl, butyryl, isobutyryl, 3,3-dimethylbutyryl, valeryl, isovaleryl, pivaloyl) and higher alkanoyl having 7 to 18 carbon atoms (e.g. heptanoyl, 2,3-dimethylpentanoyl, lauroyl, myristoyl, palmitoyl, stearoyl), lower alkoxalyl having 3 to 9 carbon atoms (e.g. methoxalyl, ethoxalyl, propoxalyl), lower cycloalkanecarbonyl having 4 to 8 carbon atoms (e.g. cyclopentanecarbonyl, cyclohexanecarbonyl, cycloheptanecarbonyl), lower($C_3$–$C_7$) cycloalkyl(lower)alkanoyl (e.g. 3-cyclopentylpropionyl), aroyl (e.g. benzoyl, naphthoyl, toluoyl, xyloyl, phthaloyl), ar(lower)alkanoyl (e.g. phenylacetyl), lower alkanesulfonyl (e.g. mesyl, ethanesulfonyl, propanesulfonyl).

Suitable alkenyloxy for $R^4$ and $R_a^4$ may be lower alkenyloxy having 2 to 6 carbon atoms (e.g. vinyloxy, allyloxy, 1-propenyloxy, 3-butenyloxy).

Suitable 2,2-dialkoxycarbonylvinylamino for $R^4$ may be 2,2-di(lower)alkoxycarbonylvinylamino (e.g. 2,2-dimethoxycarbonylvinylamino, 2,2-diethoxycarbonylvinylamino).

Suitable alkenyl for $R^5$ may be lower alkenyl having 2 to 6 carbon atoms (e.g. vinyl, allyl, 2-propenyl, 3-butenyl, 3-pentenyl, 5-hexenyl, etc.).

Quinazoline derivatives of this invention can be prepared by various processes as illustrated below.

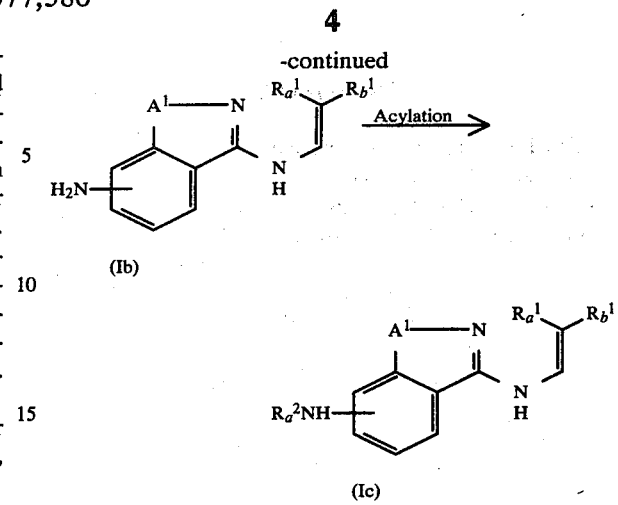

wherein
$R_a^1$, $R_b^1$, $R^2$, $R^3$, $A^1$ and $A^2$ are each as defined above,
$R_a^2$ is acyl, and
$R^7$ is alkoxy.

The processes as illustrated above are explained in the following in more detail.

Process 1:

The object compound (I) can be prepared by reacting a compound (III) or its salt with a compound (IV).

Preferred examples of the alkoxy for $R^7$ of the compound (IV) may be lower ones (e.g. methoxy, ethoxy, propoxy, etc.).

The salt of the compound (III) may be a salt with an inorganic or organic acid such as hydrochloric acid, hydrobromic acid, p-toluenesulfonic acid, etc.

The starting compounds (III) include known and novel ones. The known compounds, e.g. 4-aminoquinazoline, 2-chloro-4-aminoquinazoline, 2-hydroxy-4-aminoquinazoline and 2-methoxy-4-aminoquinazoline can be prepared by the method described in Journal of the Chemical Society (C) 1284 (1969), Chemical Abstracts 54, 24778b and 9939C (1960), and the new compounds (III) can be prepared in the similar manner thereto. The method for preparing said new compound is to be referred to Preparation of starting compounds as described hereinafter.

The reaction of this process is usually conducted in a solvent such as N,N-dimethylformamide, ethanol, propanol, isobutyl alcohol, tetrahydrofuran, diphenylether, chloroform, toluene, xylene, or the like, at a temperature range from cooling to heating.

This reaction may be carried out in the presence of a base such as alkali metal hydride (e.g. sodium hydride), alkali metal amide (e.g. sodium amide) alkali metal alkoxide (e.g. potassium t-butoxide), diazabicyclo compound (e.g. 1,5-diazabicyclo[3,4,0]nonene-5, 1,5-diazabicyclo[5,4,0]undecene-5, etc.), or the like.

When this reaction is conducted at relatively high temperature, there may be occasionally produced a ring closure compound, i.e. primidoquinazoline compound (II). Thus produced pyrimidoquinazoline compound can be transformed to quinazoline compound (I) by treating it with a strong base such as alkali metal alkoxide (e.g. sodium ethoxide). This case is also included within the scope of this process.

Process 2:

The object compound (Ib) can be prepared by reducing a compound (Ia).

The reduction can preferably be conducted by catalytic reduction.

The catalytic reduction is usually conducted at ambient temperature or under cooling in an inert solvent (e.g. N,N-dimethylformamide, ethanol, propanol, isobutyl alcohol, tetrahydrofuran, chloroform, ethyl acetate, acetic acid, etc.) by using a conventional catalyst such as Raney nickel, palladium on carbon, or the like.

Process 3:

The object compound (Ic) can be prepared by reacting a compound (Ib) with an acylating agent.

The acylating agent to be used in this reaction includes an organic acid (i.e. $R_a^2OH$, in which $R_a^2$ is as defined above) and its reactive derivative.

Suitable examples of the organic acids are to be referred to the descriptions of the suitable acyl moiety of the acylamino group for $R^2$ of the compound (II).

The suitable reactive derivative may be a conventional ones such as an acid halide (e.g. acid chloride, acid bromide, etc.), an acid azide, an acid anhydride, an activated amide, an activated ester, etc.

When free acid is used as an acylating agent, the acylation reaction may preferably be conducted in the presence of a conventional condensing agent.

The reaction is usually conducted in a solvent such as N,N-dimethylformamide, dimethylsulfoxide, tetrahydrofuran, dichloromethane, chloroform, pyridine or a mixture thereof.

The reaction can also be conducted preferably in the presence of an organic or inorganic base such as alkali metal (e.g. sodium), alkaline earth metal (e.g. calcium), alkali or alkaline earth metal hydride (e.g. sodium hydride, calcium hydride, etc.), alkali or alkaline earth metal hydroxide (e.g. sodium hydroxide, potassium hydroxide, calcium hydroxide, etc.), alkali or alkaline earth metal carbonate or bicarbonate (e.g. sodium carbonate, potassium carbonate, sodium bicarbonate), alkali or alkaline earth metal alkoxide (e.g. sodium ethoxide, lithium methoxide, magnesium methoxide), trialkylamine (e.g. triethylamine), pyridine, bicyclodiaza compound (e.g. 1,5-diazabicyclo[3,4,0]nonene-5, 1,5-diazabicyclo[5,4,0]undecene-5, etc.) and the like.

The reaction may preferably be conducted within the range of cooling to ambient temperature.

When this acylation reaction is conducted with an excess amount of the acylating agent, there may occasionally be produced N,N-diacylated compound, and this case is also included within the scope of this process.

Process 4:

The object compound (IIa) can be prepared by heating a compound (Id).

This reaction is usually conducted under heating, preferably at 160°–270° C. in the presence or absence of a solvent such as N,N-dimethylformamide, diphenylether, biphenyl, paraffin or the like. The optimum reaction conditions can be selected from the above reaction conditions according to kinds of the starting compound.

Process 5:

The object compound (IIb) can be prepared by subjecting a compound (IIa) to selective hydrolysis of the ester.

This reaction is usually conducted by heating a compound (IIa) in the presence of lithium iodide in an inert solvent such as N,N-dimethylformamide, collidine, lutidine, pyridine and the like, and then treating the resultant compound with water.

The object compound prepared by each process as mentioned above can be isolated and purified in a conventional manner.

The object compound, quinazoline derivatives (I) and (II) possess strong antiallergic activity and anti-inflammatory activity. Accordingly, the object compound of this invention is useful for the treatment of symptoms associated with allergic diseases such as allergic asthma, allergic rhinitis, urticaria, pollenosis, allergic conjunctivitis, atopic dermatitis, ulcerative colitis, alimentary allergy (e.g. milk allergy), bird fancier's disease, aphthous stomatitis and the like. For illustrating purpose, the antiallergic activity of some representative compounds of the object compounds (I) and (II) are shown in the following.

TEST I [Inhibitory effect on PCA (Passive Cutaneous Anaphylaxis) reaction]

---

(1) Test compound (a) Test compound of the formula:

-continued
(1) Test compound
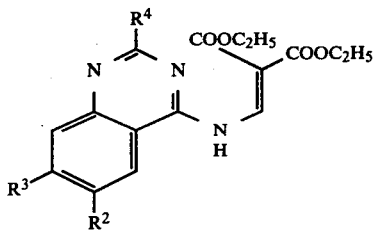
| Test compound No. | $R^2$ | $R^3$ | $R^4$ |
|---|---|---|---|
| 1 | H | H | H |
| 2 | $CH_3$ | H | H |
| 3 | $C_2H_5-$ | H | H |
| 4 | $CH_3(CH_2)_2-$ | H | H |
| 5 | $CH_3(CH_2)_3-$ | H | H |
| 6 | H | $CH_3-$ | H |
| 7 | $CH_3-$ | $CH_3-$ | H |
| 8 | $NO_2-$ | H | H |
| 9 | H | $CH_3O-$ | H |
| 10 | Ph-O- | H | H |
| 11 | $(CH_3)_2N-$ | H | H |
| 12 | $CH_3$-N(piperazinyl)-N- | H | H |
| 13 | $CH_3CONH-$ | H | H |
| 14 | $C_2H_5CONH-$ | H | H |
| 15 | $n\text{-}C_3H_7CONH-$ | H | H |
| 16 | $(CH_3)_2CHCONH-$ | H | H |
| 17 | $C_2H_5OCOCONH-$ | H | H |
| 18 | cyclohexyl-CONH- | H | H |
| 19 | Ph-CONH- | H | H |
| 20 | H | H | $CH_3O-$ |
(b) Test Compound No. 21
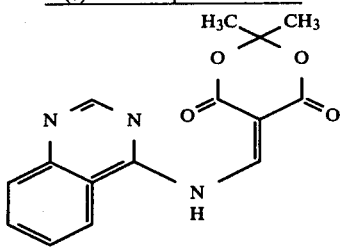
(c) Test Compound No. 22

-continued (1) Test compound

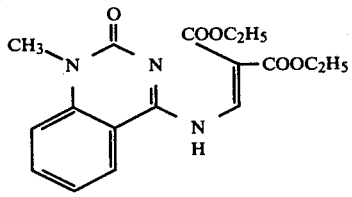

(d) Test Compound of the formula:

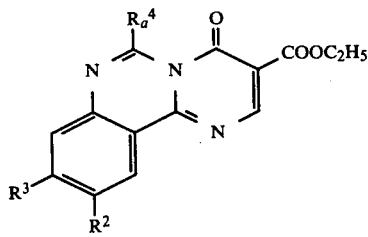

| Test Compound No. | $R^2$ | $R^3$ | $R_a^4$ |
|---|---|---|---|
| 23 | H | H | H |
| 24 | CH$_3$— | H | H |
| 25 | C$_2$H$_5$— | H | H |
| 26 | n-C$_3$H$_7$— | H | H |
| 27 | n-C$_4$H$_9$— | H | H |
| 28 | H | CH$_3$— | H |
| 29 | Cl— | H | H |
| 30 | H | Cl— | H |
| 31 | NO$_2$— | H | H |
| 32 | H | CH$_3$O— | H |
| 33 | (CH$_3$)$_2$N— | H | H |
| 34 | CH$_3$—N(piperazinyl)N— | H | H |
| 35 | CH$_3$CONH— | H | H |
| 36 | H | CH$_3$CONH— | H |
| 37 | C$_2$H$_5$—CONH— | H | H |
| 38 | n-C$_3$H$_7$CONH— | H | H |
| 39 | (CH$_3$)$_2$CHCONH— | H | H |
| 40 | (CH$_3$)$_3$CCONH— | H | H |
| 41 | n-C$_5$H$_{11}$CONH— | H | H |
| 42 | C$_2$H$_5$OCOCONH— | H | H |
| 43 | cyclohexyl-CONH— | H | H |
| 44 | phenyl-CONH— | H | H |
| 45 | phenyl-CH$_2$CONH— | H | H |
| 46 | H | H | CH$_3$— |
| 47 | H | H | HO— |
| 48 | H | H | CH$_3$O— |
| 49 | H | H | CH$_2$=CHCH$_2$O— |
| 50 | C$_2$H$_5$— | H | HO— |

-continued
| (1) Test compound |
|---|
| (e) Test Compound No. 51 |
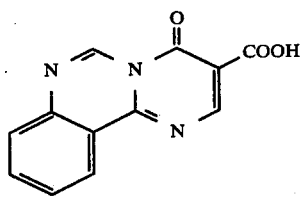
(f) Test Compound No. 52
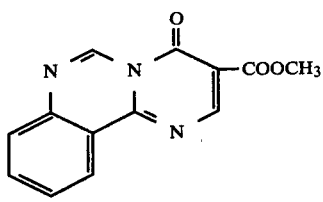
(g) Test Compound No. 53
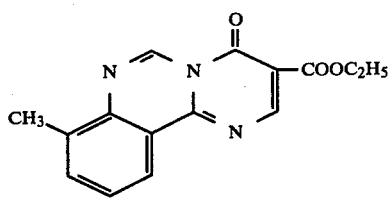
(h) Test Compound No. 54
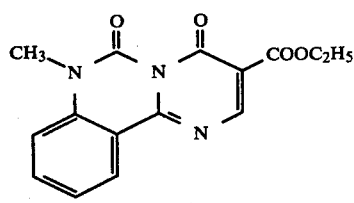
(i) Test Compound No. 55
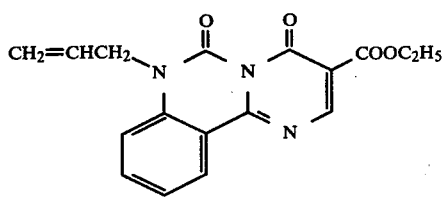
(j) Test Compound No. 56
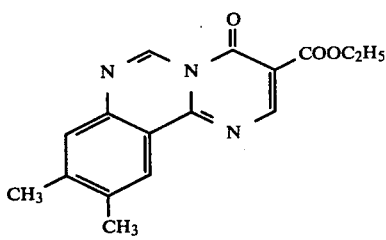
(k) Test Compound No. 57

| (1) Test compound |
|---|
| 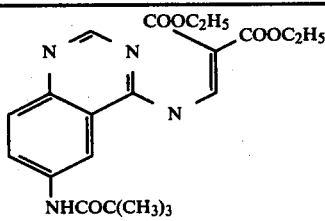 |

(2) Test method (a) Preparation of antiserum

A solution of egg albumin (2 mg) in B. pertussis-diphtheria-tetanus mixed vaccine (1 ml) was mixed with Freund incomplete adjuvant (1 ml) to give an emulsion. The emulsion was given subcutaneously in a single dose of 1 ml divided equally (0.25 ml) to the four foot pads of male SD (Sprague-Dawley) strain rats aged 8 weeks, each weighing about 300 g.

10 days after the immunization, blood samples were collected from femoral artery of the rats and allowed to stand under ice-cooling for 5 hours. The separated supernatant was centrifuged at 4° C. (10,000 r.p.m.×1 hour). The antisera thus obtained were stored at −80° C. prior to use.

(b) Inhibitory effect on P.C.A.

Male SD-strain rats aged 8 weeks, weighing 290 to 330 g, were used for PCA reaction with the homologous reaginic antiserum as prepared above. Each 0.1 ml of 64 fold diluted antiserum antiserum were injected intradermally at separate sites on the back of rats clipped free of hair, and 48 hours later, 1 ml of aqueous solution containing each 5 mg of the egg albumin and Evans blue was injected intravenously to evoke PCA reaction. Test compound was given to the animals orally 60 minutes or intravenously 5 minutes before the challenge with antigen. Control group received vehicle. Each dose group consisted of 5 animals. One hour after the challenge with antigen, the animals were sacrificed and then skinned. Dye spots caused with antiserum were investigated for their size on the reversed side of the skin, respectively. The results were expressed by percent inhibition values calcuated from averaged values of the longest and shortest diameters for each spot in comparison with those in control group.

(3) Test results

Test results are shown in the following table.

| Test Compound No. | Inhibitory effect (%) | |
|---|---|---|
| | Intravenous administration (10mg/kg) | Oral administration (100 mg/kg) |
| 1 | 100 | * |
| 2 | 100 | * |
| 3 | 100 | * |
| 4 | 85.9 | * |
| 5 | 34.8 | * |
| 6 | 100 | * |
| 7 | 42.9 | * |
| 8 | 52.7 | * |
| 9 | 56.3 | * |
| 10 | 24.4 | * |
| 11 | 100 | * |
| 12 | 51.2 | * |
| 13 | 100 | * |
| 14 | * | 77.4 |
| 15 | * | 58.1 |
| 16 | 100 | 51.6 |
| 17 | 100 | * |
| 18 | 100 | * |
| 19 | * | 73.7 |
| 20 | 37.6 | * |
| 21 | 75.4 | * |
| 22 | 100 | * |
| 23 | 100 | * |
| 24 | 100 | * |
| 25 | 100 | * |
| 26 | 100 | * |
| 27 | 100 | * |
| 28 | 100 | * |
| 29 | 100 | * |
| 30 | 100 | * |
| 31 | 64.9 | * |
| 32 | 67.5 | * |
| 33 | 100 | * |
| 34 | 100 | * |
| 35 | * | 72.7 |
| 36 | 100 | * |
| 37 | * | 74.2 |
| 38 | 100 | * |
| 39 | * | 75.8 |
| 40 | 100 | * |
| 41 | * | 100 |
| 42 | 100 | * |
| 43 | 100 | * |
| 44 | * | 49.1 |
| 45 | 100 | * |
| 46 | 76.3 | * |
| 47 | 100 | * |
| 48 | 100 | 57.5 |
| 49 | 83.1 | * |
| 50 | 39.8 | * |
| 51 | 100 | 100 |
| 52 | 100 | * |
| 53 | 85.0 | * |
| 54 | 48.4 | * |
| 55 | 91.0 | * |
| 56 | 100 | 24.2 |
| 57 | 100 | 100 |

(Note)
*: Not tested.

TEST II [Inhibitory effect on PCA (Passive Cutaneous Anaphylaxis) reaction]

| (1) Test compound |
|---|
| (a) Test compound No. 58 |
| 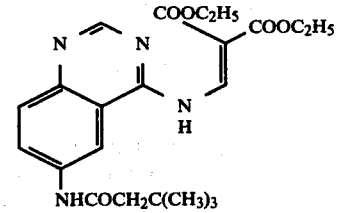 |
| (b) Test compound of the formula: |

(1) Test compound

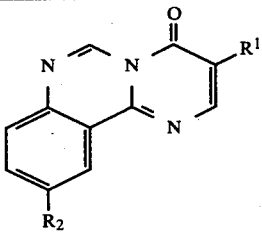

| Test compound No. | R¹ | R² |
|---|---|---|
| 59 | —COOCH₃ | —NHCOC(CH₃)₃ |
| 60 | —COOH | —NHCOC(CH₃)₃ |
| 61 | —COOC₂H₅ | —NHCOCH₂C(CH₃)₃ |
| 62 | —COOH | —NHCOCH₂C(CH₃)₃ |
| 63 | —COOH | —NHCOCH(CH₃)₂ |
| 64 | —COOH | —NHCOCH(C₂H₅)₂ |

(2) Test method

This test was carried out in substantially the same manner as described in TEST I, excepting that 32 fold diluted antiserum was used in place of 64 fold diluted antiserum for passive sensitization.

(3) Test results

Test results are shown in the following table.

| Test Compound No. | Inhibitory effect (%) Intravenous administration (1 mg/kg) | Oral administration (100 mg/kg) |
|---|---|---|
| 58 | 42.1 | * |
| 59 | 100 | * |
| 60 | 100 | 63 |
| 61 | 100 | * |
| 62 | 100 | * |
| 63 | 100 | * |
| 64 | 100 | * |

(Note)
*: Not tested.

The quinazoline derivatives (I) and (II) of this invention can be used as an active antiallergic agent either in free form or in the form of the pharmaceutically acceptable salt such as a salt with inorganic or organic acid, a salt with inorganic or organic base and a salt with an amino acid.

The object compound (I) and (II) or its pharmaceutically acceptable salt can usually be administered to mammals including human beings in the form of a conventional pharmaceutical composition such as capsule, microcapsule, tablet, granule, powder, troche, syrup, aerosol, inhalation, solution, injection, suspension, emulsion, suppository, ointment, or the like.

The pharmaceutical composition of this invention can contain various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropylstarch, sodium glycole-starch, sodium bicarbonate, calcium phosphate, calcium citrate, etc.), lubricant (e.g. magnesium stearate, aerosil, talc, sodium laurylsulfate, etc.), flavoring agent (e.g. citric acid, mentol, ammonium salt of grycyrlysine, glycine, orange powders, etc.), preservative (sodium benzoate, sodium bisulfite, methylparaben, propylparaben, etc.), stabilizer (citric acid, sodium citrate, acetic acid, etc.), suspending agent (e.g. methyl cellulose, polyvinylpyrrolidone, aluminum stearate, etc.), dispersing agent [e.g. polysolbate 80, emalgen 408 (surface active agent), emasol (surface active agent), etc.], aqueous diluting agent (e.g. water), base wax (e.g. cacao butter, polyethyleneglycol, witepsol, white petrolatum, etc.).

A dosage of the present active ingredient is to be varied depending on various factors such as weight and/or age of a patient and/or a stage of the allergic disease, and further the kind of administration route. In general, an effective dosage may be in a range of about 20–2000 mg/day for an oral route, about 2.5–250 mg/day for an intramuscular or intravenous injection, about 10–1000 mg/day for a subcutaneous injection and about 120 mg–2000 mg/day for a rectal route. The total daily amount mentioned above may be divisionally given to the patient at the interval of 6–12 hours per day. Preferable single dose of the present active ingredient may be, for example, about 10–500 mg per tablet or capsule, about 1.25–250 mg per vial or ampoule, or about 60–500 mg per suppository, and so on, and further a pharmaceutical form for an external use may be, for example, about 1–10% ointment, solution or emulsion, etc.

Starting compounds to be used in the preparation of the quinazoline derivatives of this invention can be specifically prepared in the following manner.

Preparation 1

A mixture of o-aminobenzonitrile (22.58 g) and formamide (96 ml) was refluxed for 2 hours at 220° C. After the resultant mixture was cooled to ambient temperature, precipitated crystals were separated by filtration, washed twice with a small volume of water and dried under reduced pressure to give crystalline 4-aminoquinazoline (17.0 g).

mp: 265°–268° C.

IR (Nujol) νmax: 3100, 1690, 1615, 1585 cm⁻¹

N.M.R. δppm (DMSO₄-d₆): 7.4–8.0 (5H, m), 8.30 (1H), broad d, J=8.0 Hz), 8.50 (1H, s)

The following compounds were prepared in substantially the same manner as that of the Preparation 1.

(1) 4-Amino-6-chloroquinazoline mp: >270° C.

IR (Nujol) νmax: 3100, 1680, 1570, 1548 cm⁻¹

(2) 4-Amino-7-chloroquinazoline

IR (Nujol) νmax: 3275, 3100, 1685, 1605, 1575 cm⁻¹

N.M.R. δppm (DMSO-d₆): 7.52 (1H, dd, J=2.0 and 8.0 Hz), 7.70 (1H, d, J=2.0 Hz), 7.90 (2H, broad s), 8.33 (1H, d, J=8.0 Hz), 8.40 (1H, s)

(3) 4-Amino-6-methylquinazoline mp: 266°–269° C.

IR (Nujol) νmax: 3400–3100, 1680, 1580, 1555 cm⁻¹

N.M.R. δppm (DMSO-d₆): 2.44 (3H, s), 7.56 (4H, m), 8.05 (1H, broad s), 8.30 (1H, broad s)

(4) 4-Amino-6-phenoxyquinazoline mp: 97°–99° C.

IR (Nujol) νmax: 1664, 1642, 1590 cm⁻¹

N.M.R. δppm (DMSO-d₆): 6.4–7.8 (7H, m), 7.93 (1H, d, J=9.0 Hz), 8.43 (1H, s), 10.4 (2H, s)

(5) 4-Amino-6-(N,N-dimethylamino)quinazoline mp: >270° C.

IR (Nujol) νmax: 3400-3000, 1662, 1612, 1565 cm⁻¹

N.M.R. δppm (DMSO-d₆): 2.96 (6H, s), 7.12 (1H, d, J=3.0 Hz), 7.36 (4H, m), 8.12 (1H, s)

(6) 4-Amino-6-ethylthioquinazoline mp: 158°–164° C.

IR (Nujol) νmax: 3300, 3100, 1670, 1600 cm⁻¹

N.M.R. δppm (DMSO-d₆): 1.26 (3H, t, J=8.0 Hz), 3.1 (2H, quartet, J=8.0 Hz), 7.6–8.0 (4H, m), 8.2 (1H, d, J=2.0 Hz), 8.40 (1H, s)

(7) 4-Amino-7-methoxyquinazoline

IR (Nujol) νmax: 3330, 3130, 1670, 1620, 1578 1560 cm⁻¹

N.M.R. δppm (DMSO-d₆): 3.86 (3H, s), 7.1 (2H, m), 7.56 (2H, broad s), 8.13 (1H, d, J=10.0 Hz), 8.30 (1H, s)

(8) 4-Amino-7-acetamidoquinazoline mp: >300° C.

IR (Nujol) νmax: 1675, 1628, 1570 cm⁻¹

N.M.R. δppm (DMSO-d₆): 2.16 (3H, s), 7.6 (3H, broad s), 7.9–8.3 (2H, m), 8.36 (1H, s), 10.23 (1H, broad s)

(9) 4-Amino-6-ethylquinazoline mp: 224°–227° C.

IR (Nujol) νmax: 3300, 3100, 1665, 1575, 1540 cm⁻¹

N.M.R. δppm (CDCl₃): 1.30 (3H, t, J=7.0 Hz), 1.83 (2H, s), 2.77 (2H, quartet, J=7.0 Hz), 7.4–8.0 (3H, m), 8.26 (1H, s)

(10) 4-Amino-6-butylquinazoline mp: 209°–210° C.

IR (Nujol) νmax: 3050, 1680, 1570, 1540 cm⁻¹

N.M.R. δppm (DMSO-d₆): 0.7–1.8 (7H, m), 2.7 (2H, t, J=7.0 Hz), 7.63 (4H, broad s), 8.07 (1H, s), 8.37 (1H, s)

(11) 4-Amino-8-methylquinazoline mp: 200°–214° C.

IR (Nujol) νmax: 3350, 3120, 1670, 1612, 1588 cm⁻¹

N.M.R. δppm (DMSO-d₆): 2.66 (3H, s), 7.3–8.0 (4H, m), 8.16 (1H, d, J=9.0 Hz), 8.56 (1H, s)

(12) 4-Amino-6-propylquinazoline mp: 194°–198° C.

IR (Nujol) νmax: 3320, 3100, 1660, 1570, 1550, 1500 cm⁻¹

N.M.R. δppm (DMSO-d₆): 0.93 (3H, t, J=7.0 Hz), 1.3–2.1 (2H, m), 2.73 (2H, t, J=7.0 Hz), 7.70 (2H, s), 7.75 (2H, m), 8.13 (1H, s), 8.46 (1H, s)

(13) 4-Amino-6,7-dimethylquinazoline mp: >360° C.

IR (Nujol) νmax: 3270, 3070, 1680, 1620, 1560 cm⁻¹

(14) 4-Amino-7-methylquinazoline mp: 278°–279° C.

IR (Nujol) νmax: 3330, 3150, 1670, 1620, 900, 790 cm⁻¹

N.M.R. δppm (DMSO-d₆): 2.43 (3H, s), 7.3 (1H, d, J=8.0 Hz), 7.45 (1H, s), 7.6 (2H, s), 8.1 (1H, d, J=8.0 Hz), 8.33 (1H, s)

(15) 4-Amino-6-(4-methylpiperazinyl)quinazoline mp: 229°–234° C.

IR (Nujol) νmax: 3170, 3050, 1670, 1640, 1620 cm⁻¹

N.M.R. δppm (DMSO-d₆): 2.23 (3H, s), 2.5 (4H, m), 3.26 (4H, m), 3.45 (2H, s), 7.3–7.6 (3H, m), 8.2 (1H, s)

(16) 4-Amino-6,7-dimethoxyquinazoline mp: 204°–206° C.

IR (Nujol) νmax: 3320, 1672, 1612, 1580 cm⁻¹

N.M.R. δppm (DMSO-d₆): 3.90 (6H, s), 7.1 (1H, s), 7.40 (2H, s), 7.6 (1H, s), 8.27 (1H, s)

(17) 4-Amino-6-[bis(2-hydroxyethyl)amino]quinazoline

N.M.R. δppm (DMSO-d₆): 3.53 (8H, m), 4.5 (2H, s), 7.0–7.6 (5H, m), 8.1 (1H, s)

IR (Nujol) νmax: 3380, 1660, 1618, 1575 cm⁻¹ mp: 227°–231° C.

(18) 4-Amino-7-pivalamidoquinazoline mp: 305°–307° C.

Preparation 2

A mixture of 2-amino-5-nitrobenzonitrile (48.9 g), anhydrous potassium carbonate (45.6 g), formamide (240 ml) and N,N-dimethylformamide (200 ml) was stirred for 50 minutes at 150° C. and then cooled to ambient temperature. To the resultant mixture was added a small volume of water with stirring. Precipitated crystals were separated by filtration, washed three times with water and dried under reduced pressure to give crystalline 4-amino-6-nitroquinazoline (50.1 g).

mp: >360° C.

IR (Nujol) νmax: 3350, 3200, 1680, 1620 cm⁻¹

N.M.R. δppm (DMSO-d₆): 7.76 (1H, d, J=9.0 Hz), 8.43 (1H, dd, J=3.0 and 9.0 Hz), 9.26 (1H, d, J=3.0 Hz), 8.30 (2H, m)

Preparation 3

(a) A mixture of 2,4-quinazolinedione (20 g), tri-n-propylamine (38 g) and phosphorus oxychloride (200 ml) was stirred for 40 minutes at 120° C. The resultant mixture was concentrated under reduced pressure to give a solid residue, which was extracted twice with warm 2% tri-n-propylamine-heptane solution (250 ml) and twice with 2% tri-n-propylamine-ether solution (250 ml). To the combined extracts was added a small volume of benzene to dissolve precipitated crystals. The solution was washed with 0.5 N sodium hydroxide aqueous solution, three times with water and with aqueous solution saturated with sodium chloride. The resultant solution was dried over anhydrous magnesium sulfate and concentrated under reduced pressure to give crystalline 2,4-dichloroquinazoline (20 g). After the crystals were dissolved in dioxane (140 ml), ammonia was passed through the resultant solution for 40 minutes and the resultant mixture was allowed to stand overnight. Precipitates were separated by filtration, washed twice with water and dried under reduced pressure to give crystalline 2-chloro-4-aminoquinazoline (12.4 g).

(b) To the solution of sodium metal (0.7 g) in dried allylalcohol (90 ml) was added 4-amino-2-chloroquinazoline (3.5 g) and the mixture was stirred for 5 hours at 100° C. After the resultant mixture was concentrated under reduced pressure, to the residue was added a small volume of water. The aqueous mixture was extracted twice with ethyl acetate. The organic layer was washed with water and with aqueous solution saturated with sodium chloride, dried over anhydrous magnesium sulfate and concentrated under reduced pressure to give a crystalline residue, which was recrystallized from a mixture of ethyl acetate and hexane to give crystalline 2-allyloxy-4-aminoquinazoline (2.8 g).

mp: 105°–110° C.

IR (Nujol) νmax: 3300, 3100, 1670, 1635, 1615 cm⁻¹

N.M.R. δppm (DMSO-d₆): 4.88 (2H, d, J=4.0 Hz), 5.2–5.5 (2H, m), 6.1 (1H, m), 7.2–8.3 (6H, m)

Preparation 4

(a) A mixture of 1-methylquinazoline-2,4-dione (8.8 g), tri-n-propylamine (8.6 g) and phosphorus oxychloride (80 ml) was stirred for 1 hour at 110°–120° C. The resultant mixture was cooled to ambient temperature and concentrated under reduced pressure to give a residue, which was dissolved in 2% tri-n-propylamine-chloroform solution. The solution was added dropwise to a mixture of 2 N sodium hydroxide aqueous solution and ice at alkaline pH. The aqueous layer was separated and extracted twice with chloroform. The combined chloroform layer was washed with water and with aqueous solution saturated with sodium chloride, dried over anhydrous magnesium sulfate and concentrated under reduced pressure to give crystalline 4-chloro-1-methyl-1H-quinazoline-2-one.

(b) A solution of 4-chloro-1-methyl-1H-quinazoline-2-one obtained above in methanol (50 ml) and dioxane (70 ml) was ice-cooled. After ammonia was passed through the solution for 16 minutes, the resultant solution was allowed to stand overnight at ambient temperature. Insoluble materials were filtered off and washed with methanol. The combined filtrate and washings was concentrated under reduced pressure to give a residue, which was dissolved in methanol. To the solution was dropwise added ether to give precipitates, which was separated by filtration and washed with a mixture of methanol and ether to give crystalline 4-amino-1-methyl-1H-quinazoline-2-one (4.05 g). The same crystalline compound (0.7 g) was recovered from the mother liquor in the same manner as mentioned above.

mp: 252°–262° C.

IR (Nujol) $\nu$max: 3350, 3160, 1708, 1652, 1590, 1530 cm$^{-1}$

N.M.R. $\delta$ppm (DMSO-d$_6$): 3.48 (3H, s), 3.50 (2H, broad s), 7.12–7.40 (2H, m), 7.72 (1H, t, J=8.0 Hz), 8.16 (1H, d, J=8.0 Hz)

Preparation 5

(a) A mixture of 2-bromo-4-ethylaniline (29.2 g) and cuprous cyanide (14.4 g) in dry pyridine (25.4 g) was stirred for 16 hours at 160° C. After cooling to 60° C., the resultant mixture was poured into a mixture (250 ml) of conc. aqueous ammonia and water (1:1) with stirring. To the resultant mixture was added ethyl acetate (300 ml) with stirring. Insoluble materials were filtered off. The organic layer was washed three times with water and with aqueous solution saturated with sodium chloride, dried over anhydrous magnesium sulfate and concentrated under reduced pressure to give an oily residue, to which was added benzene and concentrated under reduced pressure. These operations were repeated twice to remove pyridine. The resultant oily residue was subjected to a column chromatography using silica gel (developing solvent: a mixture of benzene and hexane (3:1)) to give 2-amino-4-ethylbenzonitrile (16.4 g).

IR (film) $\nu$max: 3460, 3370, 3225, 2200, 1620 cm$^{-1}$

N.M.R. $\delta$ppm (CCl$_4$): 1.16 (3H, t, J=7.0 Hz), 2.5 (2H, quartet, J=7.0 Hz), 4.36 (2H, s), 6.5 (1H, d, J=10.0 Hz), 7–7.4 (2H, m)

(b) To a solution of 2-amino-4-ethylbenzonitrile (39.9 g) in acetic acid (200 ml) was added potassium cyanate (24.4 g) under ice-cooling in the course of 15 minutes and stirred overnight in water bath. To the resultant mixture was added water to give precipitates, which were separated by filtration, washed with water and dried at ambient temperature. The resultant crude crystals were recrystallized from ethanol to give crystalline (2-cyano-4-ethylphenyl)urea (29.0 g).

mp: >360° C.

IR (Nujol) $\nu$max: 3450, 3350, 3250, 3200, 2220, 1660, 1620 cm$^{-1}$

N.M.R. $\delta$ppm (DMSO-d$_6$): 1.2 (3H, t, J=7.0 Hz), 2.6 (2H, quartet, J=7.0 Hz), 6.40 (2H, broad s), 7.40–7.73 (2H, m), 8.0 (1H, d, J=8.0 Hz), 8.50 (1H, broad s)

(c) To a solution of sodium metal (0.365 g) in dried methanol (300 ml) was added (2-cyano-4-ethylphenyl)urea (10 g) and the reaction mixture was heated under reflux for 5 hours and a half. The resultant mixture was concentrated under reduced pressure to give a residue, to which was added water. The resultant crystals were separated by filtration, washed with water and dried under reduced pressure to give crystalline 4-amino-6-ethyl-2-hydroxyquinazoline (9.35 g).

mp: >350° C.

IR (Nujol) $\nu$max: 3360, 3100, 1670, 1635, 1600 cm$^{-1}$

N.M.R. $\delta$ppm (DMSO-d$_6$): 1.2 (3H, t, J=8.0 Hz), 2.6 (2H, quartet, J=8.0 Hz), 7.06 (1H, d, J=8.0 Hz), 7.46 (1H, dd, J=2.0 and 8.0 Hz), 7.6–8.0 (3H, m), 11.2 (1H, s)

Preparation 6

(a) A mixture of 2-amino-5-ethylbenzoic acid (20.28 g) and ethyl chlorocarbonate (53.5 g) was stirred for 50 minutes at 100° C. and then cooled to 90° C. To the mixture was added dropwise acetyl chloride (13.81 g) in the course of 15 minutes and the reaction mixture was stirred for 2 hours at 100° C. After the resultant mixture was cooled to ambient temperature, to the mixture was added hexane and allowed to stand at ambient temperature to give crystals, which were separated by filtration, washed with hexane and dried under reduced pressure to give crystalline 6-ethyl-2H-3,1-benzoxazine-2,4(1H)-dione (19.55 g).

mp: 178°–181° C.

IR (Nujol) $\nu$max: 3230, 1760, 1690, 1615, 1605 cm$^{-1}$

N.M.R. $\delta$ppm (CDCl$_3$): 1.23 (3H, t, J=8.0 Hz), 2.7 (2H, quartet, J=8.0 Hz), 7.0–8.0 (3H, m), 9.3 (1H, s)

(b) A mixture of 6-ethyl-2H-3,1-benzoxazine-2,4(1H)-dione (19.55 g) and urea (6.18 g) in dry N,N-dimethylformamide (98 ml) was heated under reflux for 3 hours and 40 minutes. After the reaction mixture was cooled to ambient temperature, to the mixture was added water with stirring to give crystals, which were separated by filtration, washed with water and dried under reduced pressure to give crystalline 6-ethyl-1H,3H-quinazoline-2,4-dione (11.74 g).

mp: 271°–274° C.

IR (Nujol) $\nu$max: 3310, 3160, 3030, 1720, 1685, 1620 cm$^{-1}$

N.M.R. $\delta$ppm (DMSO-d$_6$): 1.2 (3H, t, J=8.0 Hz), 2.65 (2H, quartet, J=8.0 Hz), 7.18 (1H, d, J=8.0 Hz), 7.56 (1H, dd, J=2.0 and 8.0 Hz), 7.8 (1H, d, J=2.0 Hz), 12.0 (2H, s)

(c) A mixture of 6-ethyl-1H,3H-quinazoline-2,4-dione (3.78 g), tri-n-propylamine (5.72 g) and phosphorus oxychloride (38 ml) was stirred for 40 minutes at 120° C. and then cooled to ambient temperature. The reaction mixture was concentrated under reduced pressure to give a residue, to which was added warm (50°–60° C.) 2% tri-n-propylamine-heptane solution (50 ml) with stirring. The supernatant was separated and the solid residue was treated three times in substantially same manner as mentioned above. To the combined heptane layer was added benzene. The resultant mixture was washed twice with 5% sodium hydroxide aqueous solution (50 ml), three times with water and with aqueous solution saturated with sodium chloride. The mixture was dried over anhydrous magnesium sulfate and concentrated under reduced pressure to give crystalline-2,4-dichloro-6-ethylquinazoline (4.07 g).

mp: 80°–83° C.

IR (Nujol) $\nu$max: 1530, 1480, 1450, 1410, 1160, 1110 cm$^{-1}$

N.M.R. $\delta$ppm (CDCl$_3$): 1.4 (3H, t, J=8.0 Hz), 2.93 (2H, quartet, J=8.0 Hz), 7.96 (2H, broad s), 8.1 (1H, s)

(d) A solution of 2,4-dichloro-6-ethylquinazoline (10.8 g) in methanol and chloroform (70 ml) was cooled with ice-water. Ammonia was passed through the reaction mixture for 20 minutes and the mixture was allowed to stand for 18 hours at ambient temperature. The resultant mixture was concentrated under reduced pressure to give a residue, to which was added water and heated to 50°–60° C. with stirring. The precipitates was separated by filtration, washed with hot water and recrystallized from dioxane to give crystalline 4-amino-2-chloro-6-ethylquinazole (8.3 g). Crystals (0.7 g) of the same compound were obtained by treating the mother liquor in substantially the same manner as mentioned above.

mp: 244°–246° C.

IR (Nujol) νmax: 3380, 3340, 3120, 1660, 1570, 1540 cm$^{-1}$

N.M.R. δppm (DMSO-d$_6$): 1.3 (3H, t, J=8.0 Hz), 2.8 (2H, quartet, J=8.0 Hz), 7.5–7.9 (2H, m), 8.16 (1H, s), 8.3 (2H, broad s)

(e) To a solution of sodium metal (1.19 g) in methanol (270 ml) was added 4-amino-2-chloro-6-ethylquinazoline (9.01 g). The reaction mixture was heated under reflux for 7 hours and heated for 38 hours at 60° C. The resultant mixture was concentrated under reduced pressure to give a residue, to which was added water under warming with stirring. The precipitates were separated by filtration and dried under reduced pressure to give crystalline 4-amino-6-ethyl-2-methoxyquinazoline (6.77 g).

mp: 168°–170° C.

IR (Nujol) νmax: 3300, 1630, 1580 cm$^{-1}$

N.M.R. δppm (DMSO-d$_6$): 1.30 (3H, t, J=7.0 Hz), 2.76 (2H, quartet, J=7.0 Hz), 4.06 (3H, s), 7.70 (2H, m), 8.36 (1H, broad s), 9.20 (2H, m)

Preparation 7

A mixture of iron (113.9 g), conc. hydrochloric acid (57 ml) and water (2.3 liters) was stirred at 95° C. for 20 minutes. To the mixture was added during 10 minutes 4-amino-6-nitroquinazoline (114.1 g). The reaction mixture was stirred at 95° C. for an hour and a half and then filtered. The filter cake was washed with hot water. The combined filtrate and washings were concentrated under reduced pressure to give a residue, to which was added a small volume of ethanol to give precipitates. The precipitates were separated by filtration and dried to give 4,6-diaminoquinazoline hydrochloride (94.8 g). The same compound (4.3 g) was recovered from the mother liquor in the same manner as mentioned above.

IR (Nujol) νmax: 3310, 1665, 1610, 1560 cm$^{-1}$

Preparation 8

A mixture of 4,6-diaminoquinazoline hydrochloride (1.97 g), sodium hydrogen carbonate (6.72 g) and pyridine (20 ml) was stirred under ice-cooling. To the mixture was added dropwise during 30 minutes methanesulfonyl chloride (4.58 g) under ice-cooling. The reaction mixture was stirred for an hour under ice-cooling and for 4 hours at ambient temperature. To the mixture was added ice-water. The resultant mixture was stirred for about five minutes and concentrated under reduced pressure. To the residue was added a mixture of chloroform and methanol. The mixture was stirred under heating. Insoluble materials were removed by filtration and then the filtrate was concentrated under reduced pressure to give crude crystals, to which was added a mixture of chloroform and methanol (4:1). The mixture was stirred under heating to give crystals, which were separated by filtration to give crystalline 4-amino-6-methanesulfonamidoquinazoline (1.45 g).

mp: 287°–290° C.

IR (Nujol) νmax: 3350, 3150, 1660, 1615 cm$^{-1}$

N.M.R. δppm (DMSO-d$_6$): 3.3 (3H, s), 7.7–8.33 (4H, m), 8.83 (1H, s), 9.8 (2H, s)

Preparation 9

To a mixture of 4,6-diaminoquinazoline hydrochloride (10.0 g), tripropylamine (17.61 g) and dry pyridine (100 ml) was added dropwise during 35 minutes 3,3-dimethylbutyryl chloride (10.34 g) under ice-cooling. The reaction mixture was stirred for 2 hours at the same temperature. To the resultant mixture was added ice-water. The mixture was stirred for 5 minutes and then concentrated under reduced pressure. To the residue was added water and sodium hydrogen carbonate (13.0 g) little by little to give precipitates, which were separated by filtration, washed with water and dried. Thus obtained crude crystals were dissolved in a mixture of chloroform and methanol under heating. After insoluble materials were removed by filtration, the filtrate was concentrated under reduced pressure to give a residue, which was suspended in 5% methanol-chloroform solution (70 ml). After stirring under heating, the suspension was filtered to give crystalline 4-amino-6-(3,3-dimethylbutyramido)quinazoline (8.5 g).

mp: 273°–274° C.

IR (Nujol) νmax: 3330, 3220, 1685, 1650 cm$^{-1}$

N.M.R. δppm (DMSO-d$_6$): 1.06 (9H, s), 2.26 (2H, s), 7.6 (2H, s), 7.63 (1H, d, J=8.0 Hz), 7.83 (1H, dd, J=2.0 and 8.0 Hz), 8.4 (1H, s), 8.4 (1H, d, J=2.0 Hz), 10.03 (1H, s)

Preparation 10

The following compounds were prepared in substantially the same manner as that of Preparation 9.

(1) 4-Amino-6-pivalamidoquinazoline mp: 269°–273° C.

IR (Nujol) νmax: 3325, 3175, 1670, 1580, 1560, 1525 cm$^{-1}$

N.M.R. δppm (DMSO-d$_6$): 1.23 (9H, s), 7.5 (2H, s), 7.56 (1H, d, J=9.0 Hz), 7.80 (1H, dd, J=2.0 and 9.0 Hz), 8.3 (1H, s), 8.35 (1H, s), 9.4 (1H, s)

(2) 4-Amino-6-(2,3-dimethylpentanamido)quinazoline mp: 240°–243° C.

Preparation 11

To a mixture of 4,6-diaminoquinazoline hydrochloride (1.97 g), tripropylamine (2.60 g) and dry pyridine (20 ml) in an ice-bath was added dropwise during 10 minutes 2-ethylbutyryl chloride (1.75 g). The mixture was stirred for 3 hours at the same temperature. Crushed ice was added to the reaction mixture. The mixture was stirred for 5 minutes and concentrated under reduced pressure. After the addition of water (50 ml), sodium hydrogen carbonate (3.36 g) was added in small portions to the residue to give precipitates which were separated by filtration, washed with water and dried. The crude crystals were dissolved in a mixture of chloroform and methanol under heating. After insoluble materials were removed by filtration, the filtrate was concentrated under reduced pressure to give a residue, which was suspended in ethyl acetate. After stirring under heating, the suspension was filtered to give crystalline 4-amino-6-(2-ethylbutyramido)quinazoline (1.20 g).

mp. 248°–250° C.

IR (Nujol) νmax: 3320, 3100, 1660, 1570, 1535 cm$^{-1}$

N.M.R. δppm (DMSO-d$_6$): 9.2 (6H, t, J=6.0 Hz), 1.34–1.88 (4H, m), 2.08–2.44 (1H, m), 7.2 (2H, s), 7.6 (1H, d, J=10.0 Hz), 7.8 (1H, dd, J=3.0, 10.0 Hz), 8.34 (1H, s), 8.38 (1H, d, J=3.0 Hz), 10.02 (1H, s)

Preparation 12

A mixture of 4,6-diaminoquinazoline hydrochloride (10 g) and tripropylamine (17.6 g) in dry pyridine (100 ml) was stirred in an ice-bath for 1 hour. To the mixture was added dropwise during 40 minutes isobutyric anhydride (8.85 g). The mixture was stirred for 1 hour at 5° C. Crushed ice was added to the reaction mixture. The mixture was stirred for 5 minutes and concentrated under reduced pressure to give a residue which was dissolved in water. After insoluble materials were removed by filtration, the filtrate was adjusted to pH 8–9 with aqueous sodium bicarbonate solution and concentrated under reduced pressure to give a residue which was dissolved in a mixture of chloroform and methanol. The solution was filtered and concentrated under reduced pressure to give a crystalline residue which was suspended in ethyl acetate. The suspension was filtered to give 4-amino-6-(2-methylpropionamido)-quinazoline (5.05 g).

mp. 280°–283° C.

IR (Nujol) $\nu$max: 3260, 3120, 1655, 1575, 1510 cm$^{-1}$

N.M.R. $\delta$ppm (DMSO-d$_6$): 1.12 (6H, d, J=7.0 Hz), 2.5–2.8 (1H, m), 7.5 (2H, s), 7.5 (1H, d, J=9.0 Hz), 7.85 (1H, dd, J=2.0, 9.0 Hz), 8.3 (1H, s), 8.4 (1H, d, J=2.0 Hz), 10.03 (1H, s)

Preparation 13

A mixture of 4,6-diaminoquinazoline hydrochloride (12 g) and tripropylamine (31.7 g) in dry pyridine (120 ml) was stirred in an ice-bath for 1 hour. Cyclohexanecarbonyl chloride (12.1 g) was added dropwise during 4 hours and 20 minutes to the mixture at 70° C. The mixture was stirred for additional 1 hour at 5° C. Crushed ice was added to the reaction mixture. The mixture was stirred for 1 hour and concentrated under reduced pressure. After addition of water, the mixture was adjusted to pH 8 with sodium hydrogen carbonate to give precipitates which were separated by filtration, washed with water and dried. The precipitates were dissolved in a mixture of chloroform and methanol under heating. Insoluble materials were removed by filtration. The filtrate was concentrated under reduced pressure to give crystalline 4-amino-6-cyclohexanecarboxamidoquinazoline (9.25 g).

mp. 301°–303° C.

IR (Nujol) $\nu$max: 3700–3100, 1650, 1585, 1560, 1510 cm$^{-1}$

N.M.R. $\delta$ppm (DMSO-d$_6$): 1.0–2.0 (10H, m), 2.4–2.8 (1H, m), 7.53 (2H, s), 7.6 (1H, d, J=8.0 Hz), 7.78 (1H, dd, J=2.0, 8.0 Hz), 8.3 (1H, s), 8.43 (1H, d, J=2.0 Hz), 10.0 (1H, s)

Preparation 14

A mixture of 4,6-diaminoquinazoline hydrochloride (10 g) and tripropylamine (26.4 g) in dry pyridine (100 ml) was stirred in an ice-bath for 20 minutes. To the mixture was added dropwise during 1.5 hours 3-cyclopentylpropionyl chloride (12.2 g). The mixture was stirred in an ice-bath for 1.5 hours. Crushed ice was added to the reaction mixture. The mixture was stirred for 5 minutes and concentrated under reduced pressure. After addition of water, sodium hydrogen carbonate was added in small portions to the mixture to give precipitates which were separated by filtration, washed with water and dried. The crude crystals were dissolved in a mixture of chloroform and methanol under heating. After the filtration of insoluble materials, the filtrate was treated with activated charcoal and concentrated under reduced pressure to give a residue. The residue was suspended in ethyl acetate. The suspension was stirred for 1 hour under heating and filtered to give crystalline 4-amino-6-(3-cyclopentylpropionamido)-quinazoline (7.2 g).

mp. 279°–283° C.

IR (Nujol) $\nu$max: 3280, 3120, 1660, 1565, 1510 cm$^{-1}$

N.M.R. $\delta$ppm (DMSO-d$_6$): 0.7–2.16 (11H, m), 2.46 (2H, t, J=6.0 Hz), 7.6 (2H, m), 7.66 (1H, d, J=9.0 Hz), 7.93 (1H, d, J=9.0 Hz), 8.33 (1H, s), 8.50 (1H, s), 10.40 (1H, s)

The following Examples are given for the purpose of illustrating this invention.

EXAMPLE 1

A mixture of 4-aminoquinazoline (11.6 g) and diethyl ethoxymethylenepropanedioate (19.0 g) in N,N-dimethylformamide (40 ml) was stirred for 1 hour and 20 minutes at 160° C. and then cooled to 0° C. to precipitate crystals. To the mixture was added small volume of water with stirring. The crystals were separated by filtration, washed with water, dried overnight under reduced pressure and dissolved in ethyl acetate. The resultant solution was dried over anhydrous magnesium sulfate and recrystallized from a mixture of ethyl acetate and hexane to give crystalline diethyl [(4-quinazolinylamino)methylene]propanedioate (22.7 g).

mp: 115°–117° C.

IR (Nujol) $\nu$max: 1735, 1660, 1628 cm$^{-1}$

N.M.R. $\delta$ppm (CDCl$_3$): 1.36 (3H, t, J=7.0 Hz), 1.40 (3H, t, J=7.0 Hz), 4.36 (4H, m), 7.5–8.2 (4H, m), 8.96 (1H, s), 9.40 (1H, d, J=12.0 Hz), 12.3 (1H, broad d, J=12 Hz)

EXAMPLE 2

The following compounds were prepared in substantially the same manner as that of Example 1.

(1) Diethyl [(6-phenoxy-4-quinazolinylamino)methylene]-propanedioate.

mp: 121°–123° C. (recrystallized from a mixture of chloroform, ethyl acetate and hexane)

IR (Nujol) $\nu$max: 1720, 1625, 1617, 1608, 1580 cm$^{-1}$

N.M.R. $\delta$ppm (CDCl$_3$): 1.40 (6H, t, J=8.0 Hz), 4.33 (2H, quartet, J=8.0 Hz), 4.37 (2H, quartet, J=8.0 Hz), 7.0–7.6 (7H, m), 8.06 (1H, d, J=9.0 Hz), 8.90 (1H, s), 9.33 (1H, d, J=12.0 Hz), 12.16 (1H, d, J=12.0 Hz)

(2) Diethyl [(6-dimethylamino-4-quinazolinylamino)-methylene]propanedioate mp: 156°–158° C. (recrystallized from a mixture of chloroform and hexane)

IR (Nujol) $\nu$max: 1720, 1652, 1628, 1600 cm$^{-1}$

N.M.R. $\delta$ppm (CDCl$_3$): 1.36 (6H, m), 3.04 (6H, s), 4.34 (4H, m), 6.50 (1H, d, J=3.0 Hz), 7.34 (1H, dd, J=3.0 and 9.0 Hz), 7.72 (1H, d, J=9.0 Hz), 8.60 (1H, s), 9.24 (1H, d, J=11.0 Hz), 11.90 (1H, d, J=11.0 Hz)

(3) Diethyl [(6-ethylthio-4-quinazolinylamino)methylene]propanedioate mp: 103°–106° C. (recrystallized from a mixture of ethyl acetate and hexane)

IR (Nujol) $\nu$max: 1722, 1650, 1624, 1600 cm$^{-1}$

N.M.R. $\delta$ppm (CDCl$_3$): 1.3–1.8 (9H, m), 3.14 (2H, quartet, J=8.0 Hz), 4.2–4.7 (4H, m), 7.7–8.1 (3H, m), 8.90 (1H, s), 9.3 (1H, d, J=12.0 Hz), 12.4 (1H, d, J=12.0 Hz)

(4) Diethyl [(7-methoxy-4-quinazolinylamino)methylene]propanedioate mp: 134°–138° C. (recrystallized from a mixture of ethyl acetate and hexane)

IR (Nujol) $\nu$max: 1736, 1630, 1572 cm$^{-1}$

N.M.R. $\delta$ppm (CDCl$_3$): 1.40 (3H, t, 7.0 Hz), 1.43 (3H, t, J=7.0 Hz), 3.96 (3H, s), 4.36 (4H, m), 7.1–7.4 (2H, m), 7.83 (1H, d, J=9.0 Hz), 8.87 (1H, s), 9.30 (1H, d, J=12.0 Hz), 12.2 (1H, d, J=12.0 Hz)

(5) Diethyl [(7-acetamido-4-quinazolinylamino)methylene]propanedioate

IR (Nujol) $\nu$max: 3420, 1720, 1695, 1655, 1630, 1585 cm$^{-1}$

N.M.R. δppm (CDCl$_3$-DMSO-d$_6$): 1.36 (3H, t, J=7.0 Hz), 1.43 (3H, t, J=7.0 Hz), 2.23 (3H, s), 4.30 (4H, m), 7.93 (2H, m), 8.34 (1H, m), 8.90 (1H, s), 9.30 (1H, d, J=12 Hz), 10.27 (1H, s), 12.2 (1H, d, J=12 Hz)

(6) Diethyl [(2-hydroxy-4-quinazolinylamino)methylene]propanedioate mp: 265°–268° C. (recrystallized from a mixture of N,N-dimethylformamide and water)

IR (Nujol) νmax: 1702, 1660, 1630, 1585, 1575 cm$^{-1}$

N.M.R. δppm (CDCl$_3$): 1.40 (6H, m), 4.40 (4H, m), 7.3–8.0 (4H, m), 9.24 (1H, d, J=11.0 Hz), 12.3 (1H, d, J=11.0 Hz), 12.90 (1H, s)

(7) Diethyl [(2-methoxy-4-quinazolinylamino)methylene]propanedioate mp: 129°–135° C. (recrystallized from a mixture of ethyl acetate and hexane)

IR (Nujol) νmax: 1692, 1645, 1630, 1608, 1568 cm$^{-1}$

N.M.R. δppm (CDCl$_3$): 1.40 (3H, t, J=7.0 Hz), 1.46 (3H, t, J=7.0 Hz), 4.16 (3H, s), 4.32 (4H, m), 7.3–8.0 (4H, m), 9.30 (1H, d, J=11.0 Hz), 12.3 (1H, d, J=11.0 Hz)

(8) Diethyl [(2-allyloxy-4-quinazolinylamino)methylene]propanedioate mp: 117°–119° C. (recrystallized from a mixture of ethyl acetate and hexane)

IR (Nujol) νmax: 1672, 1640, 1620, 1560 cm$^{-1}$

N.M.R. δppm (CDCl$_3$): 1.40 (3H, t, J=7.0 Hz), 1.45 (3H, t, J=7.0 Hz), 4.40 (4H, m), 5.0–6.5 (5H, m), 7.3–8.0 (4H, m), 9.30 (1H, d, J=12.0 Hz), 12.3 (1H, d, J=12.0 Hz)

(9) Diethyl [(2-methyl-4-quinazolinylamino)methylene]propanedioate

IR (Nujol) νmax: 1680, 1640, 1620, 1600, 1550 cm$^{-1}$

N.M.R. δppm (CDCl$_3$): 1.40 (6H, m), 2.76 (3H, s), 4.33 (4H, m), 7.44–8.0 (4H, m), 9.34 (1H, d, J=12.0 Hz), 12.14 (1H, d, J=12.0 Hz)

(10) Diethyl [(2-dimethylamino-4-quinazolinylamino)methylene]propanedioate mp: 126°–128° C. (recrystallized from ethanol)

IR (Nujol) νmax: 3250, 1695, 1640, 1610, 1565 cm$^{-1}$

N.M.R. δppm (CDCl$_3$): 1.40 (6H, m), 3.26 (6H, s), 4.37 (4H, m), 7.0–7.77 (4H, m), 9.27 (1H, d, J=12 Hz), 11.90 (1H, d, J=12 Hz)

(11) Diethyl [(2-hydroxy-6-ethyl-4-quinazolynylamino)methylene]propanedioate mp: 267°–270° C. (recrystallized from a mixture of chloroform and methanol)

IR (Nujol) νmax: 1720, 1665, 1615, 1588 cm$^{-1}$

N.M.R. δppm (CDCl$_3$): 1.16–1.76 (9H, m), 2.83 (2H, quartet, J=8.0 Hz), 4.30 (4H, m), 7.56 (3H, broad s), 9.26 (1H, d, J=11.5 Hz), 12.26 (1H, d, J=11.5 Hz), 12.90 (1H, s)

(12) Diethyl [(2-methoxy-6-ethyl-4-quinazolinylamino)methylene]propanedioate mp: 149°–152° C. (recrystallized from ethyl acetate)

IR (Nujol) νmax: 1730, 1652, 1635, 1622, 1575 cm$^{-1}$

N.M.R. δppm (CDCl$_3$): 1.20–1.67 (9H, m), 2.86 (2H, quartet, J=8.0 Hz), 4.17 (3H, s), 4.36 (4H, m), 7.63 (3H, m), 9.23 (1H, d, J=11.5 Hz), 12.16 (1H, d, J=11.5 Hz)

EXAMPLE 3

A mixture of 4-amino-6-ethylquinazoline (6.35 g) and diethyl ethoxymethylenepropanedioate (9.52 g) in N,N-dimethylformamide (25 ml) was stirred for 3 hours at 110° C. and then cooled to ambient temperature. A small volume of water was added to the resultant mixture to precipitate crystals, which were separated by filtration and washed with water. The crystals were dissolved in chloroform, washed with an aqueous solution saturated with sodium chloride, dried over anhydrous magnesium sulfate and concentrated under reduced pressure to give a crystalline residue, which was recrystallized from a mixture of ethyl acetate and hexane to give crystalline diethyl [(6-ethyl-4-quinazolinylamino)methylene]propanedioate (8.40 g). Further, crystals (2.75 g) of the same compound were recovered from the mother liquor in the same manner as mentioned above.

mp: 104°–106° C.

IR (Nujol) νmax: 3250, 1700, 1645, 1610, 1560 cm$^{-1}$

N.M.R. δppm (CDCl$_3$): 1.2–1.5 (9H, m), 2.96 (2H, quartet, J=7.0 Hz), 4.1–4.7 (4H, m), 7.7–8.1 (3H, m), 8.95 (1H, s), 9.4 (1H, d, J=12.0 Hz), 12.3 (1H, d, J=12.0 Hz)

EXAMPLE 4

The following compounds were prepared in substantially the same manner as that of Example 3.

(1) Diethyl [(6-methyl-4-quinazolinylamino)methylene]propanedioate mp: 137°–139° C. (recrystallized from a mixture of chloroform and hexane)

IR (Nujol) νmax: 1735, 1655, 1630, 1615 cm$^{-1}$

N.M.R. δppm (CDCl$_3$): 1.40 (3H, t, J=8.0Hz), 1.46 (3H, t, J=8.0 Hz), 2.63 (3H, s), 4.33 (2H, quartet, J=8.0 Hz), 4.46 (2H, quartet, J=8.0 Hz), 7.8–8.1 (3H, m), 8.93 (1H, s), 9.4 (1H, d, J=12.0 Hz), 12.16 (1H, d, J=12.0 Hz)

(2) Diethyl [(6-butyl-4-quinazolinylamino)methylene]propanedioate mp: 83°–85° C. (recrystallized from a mixture of ethyl acetate and hexane)

IR (Nujol) νmax: 3220, 1730, 1650, 1630, 1610, 1560 cm$^{-1}$

N.M.R. δppm (CCl$_4$): 0.7–2.1 (13H, m), 2.86 (2H, t, J=7.0 Hz), 4.26 (2H, quartet, J=7.0 Hz), 4.36 (2H, quartet, J=7.0 Hz), 7.6–8.0 (3H, m), 8.76 (1H, s), 9.23 (1H, d, J=12.0 Hz), 12.2 (1H, d, J=12.0 Hz)

(3) Diethyl [(8-methyl-4-quinazolinylamino)methylene]propanedioate mp: 121°–123° C. (recrystallized from a mixture of ethyl acetate and hexane)

IR (Nujol) νmax: 1705, 1650, 1618, 1605, 1580 cm$^{-1}$

N.M.R. δppm (CDCl$_3$): 1.40 (3H, t, J=7.0 Hz), 1.43 (3H, t, J=7.0 Hz), 2.73 (3H, s), 4.37 (4H, m), 7.4–7.9 (3H, m), 8.97 (1H, s), 9.33 (1H, d, J=12.0 Hz), 12.26 (1H, d, J=12.0 Hz)

(4) Diethyl [(6-propyl-4-quinazolinylamino)methylene]propanedioate mp: 96°–99° C. (recrystallized from a mixture of ethyl acetate and hexane)

IR (Nujol) νmax: 3200, 1690, 1640, 1630, 1600, 1550 cm$^{-1}$

N.M.R. δppm (CCl$_4$): 0.8–2.2 (11H, m), 2.9 (2H, t, J=8.0 Hz), 4.0–4.7 (4H, m), 7.5–8.0 (3H, m), 8.8 (1H, s), 9.23 (1H, d, J=12 Hz), 12.23 (1H, d, J=12.0 Hz)

(5) Diethyl [(7-methyl-4-quinazolinylamino)methylene]propanedioate mp: 118°–120° C. (recrystallized from a mixture of chloroform and hexane)

IR (Nujol) νmax: 3250, 1685, 1640, 1620, 1605, 1560 cm$^{-1}$

N.M.R. δppm (DMSO-d$_6$): 1.2 (3H, t, J=7.0 Hz), 1.26 (3H, t, J=7.0 Hz), 3.2 (3H, s), 4.15 (2H, quartet, J=7.0 Hz), 4.26 (2H, quartet, J=7.0 Hz), 7.4–8.0 (3H, m), 8.8 (1H, s), 9.06 (1H, d, J=12.0 Hz), 11.53 (1H, d, J=12.0 Hz)

(6) Diethyl [(6-{bis(2-hydroxyethyl)amino}-4-quinazolinylamino)methylene]propanedioate mp: 194°–195° C. (recrystallized from chloroform)

IR (Nujol) νmax: 3300, 1720, 1648, 1630, 1605 cm$^{-1}$

N.M.R. δppm (DMSO-d$_6$): 1.30 (3H, t, J=7.0 Hz), 1.33 (3H, t, J=7.0 Hz), 3.60 (8H, m), 4.26 (4H, m), 4.80 (2H, m), 6.73 (1H, broad s), 7.7 (2H, m), 8.63 (1H, s), 9.16 (1H, d, J=12.0 Hz), 11.56 (1H, d, J=12.0 Hz)

EXAMPLE 5

A mixture of 4-amino-6-(4-methylpiperazinyl)-quinazoline (2.19 g) and diethyl ethoxymethylenepropanedioate (2.13 g) in isobutylalcohol (9 ml) was stirred for 2 hours and 25 minutes at 100° C. and then cooled to ambient temperature. The resultant mixture was concentrated under reduced pressure to give a residue, which was recrystallized from ethanol to give crystalline diethyl [{6-(4-methylpiperazinyl)-4-quinazolinylamino}methylene]propanedioate (1.58 g).

mp: 154°–159° C.

IR (Nujol) νmax: 3300, 1760, 1740, 1690, 1650, 1630, 1600 cm$^{-1}$

N.M.R. δppm (CDCl$_3$): 1.40 (3H, t, J=7.0 Hz), 1.43 (3H, t, J=7.0 Hz), 2.40 (3H, s), 2.63 (4H, m), 3.43 (4H, m), 4.33 (4H, m), 7.0 (1H, d, J=3.0 Hz), 7.56 (1H, dd, J=3.0 and 9.0 Hz), 7.86 (1H, d, J=9.0 Hz), 8.76 (1H, s), 9.30 (1H, d, J=12.0 Hz)

EXAMPLE 6

The following compound was prepared by substantially the same manner as that of Example 5.

Diethyl [(6,7-dimethoxy-4-quinazolinylamino)methylene]propanedioate mp: 226°–229° C. (recrystallized from a mixture of chloroform and hexane)

IR (Nujol) νmax: 1675, 1636, 1620, 1608, 1550 cm$^{-1}$

N.M.R. δppm (CDCl$_3$): 1.37 (3H, t, J=7.0 Hz), 1.40 (3H, t, J=7.0 Hz), 4.03 (3H, s), 4.06 (3H, s), 4.33 (4H, m), 7.03 (1H, s), 7.23 (1H, s), 8.76 (1H, s), 9.30 (1H, d, J=12.0 Hz), 12.0 (1H, d, J=12.0 Hz)

EXAMPLE 7

A mixture of 4-amino-1-methyl-1H-quinazoline-2-one (4.20 g) and diethyl ethoxymethylenepropanedioate (5.7 g) in N,N-dimethylformamide (20 ml) was stirred for 3 hours at 150° C. and then cooled to ambient temperature. Precipitated crystals were separated by filtration, washed with water and dried under reduced pressure to give crude crystals, which were recrystallized from a mixture of chloroform, ethyl acetate and hexane to give crystalline diethyl [(1-methyl-1H-2-oxo-4-quinazolinylamino)methylene]propanedioate (4.0 g).

mp: 182°–185° C.

IR (Nujol) νmax: 1725, 1700, 1675, 1635, 1610, 1588 cm$^{-1}$

N.M.R. δppm (CDCl$_3$): 1.30 (3H, t, J=7.0 Hz), 1.40 (3H, t, J=7.0 Hz), 3.66 (3H, s), 4.33 (4H, m), 7.2–7.5 (2H, m), 7.6–8.0 (2H, m), 9.16 (1H, d, J=12.0 Hz), 12.23 (1H, d, J=12.0 Hz)

EXAMPLE 8

A mixture of 2,4-diaminoquinazoline (3 g), diethyl ethoxymethylenepropanedioate (8.5 g) in N,N-dimethylformamide (15 ml) was stirred for 2 hours and 45 minutes at 150° C. and then cooled to ambient temperature. To the resultant mixture was added a small volume of water to give crystals, which were separated by filtration, washed with water and dried under reduced pressure. The resultant crude crystals were subjected to a column chromatography using silica gel (developing solvent: a mixture of chloroform and ethyl acetate) to give crystalline tetraethyl 2,2-[2,4-quinazolinediylbis-(iminomethylidyne)]bispropanedioate (1.8 g).

mp: 146°–148° C.

IR (Nujol) νmax: 3250, 1700, 1680, 1650, 1640, 1630, 1600, 1545 cm$^{-1}$

N.M.R. δppm (CDCl$_3$): 1.43 (12H, m), 4.40 (8H, m), 7.33–8.00 (4H, m), 9.23 (1H, d, J=12.0 Hz), 9.25 (1H, d, J=13.0 Hz), 11.0 (1H, d, J=13.0 Hz), 12.30 (1H, d, J=12.0 Hz)

EXAMPLE 9

A mixture of 4-aminoquinazoline (2.9 g) and 2,2-dimethyl-5-ethoxymethylene-1,3-dioxane-4,6-dione (4.46 g) in N,N-dimethylformamide (20 ml) was stirred for 1 hour and 10 minutes at 110° C. The resultant mixture was cooled to ambient temperature and allowed to stand overnight to give crystals, which were separated by filtration and washed with a mixture of ethyl acetate and hexane to give crystalline 2,2-dimethyl-5-[(4-quinazolinyl)amino]methylene-1,3-dioxane-4,6-dione (4.1 g).

mp: 191°–193° C.

IR (Nujol) νmax: 1732, 1680, 1620, 1608 cm$^{-1}$

N.M.R. δppm (CDCl$_3$): 1.80 (6H, s), 7.60–8.17 (4H, m), 9.03 (1H, s), 9.67 (1H, d, J=12.2 Hz), 11.43 (1H, broad d, J=12.2 Hz)

EXAMPLE 10

A mixture of 4-amino-6-nitroquinazoline (57.0 g) and diethyl ethoxymethylenepropanedioate (130 g) in anhydrous N,N-dimethylformamide (570 ml) was cooled at 5° C. To the reaction mixture was added sodium hydride (65.5% in mineral oil) (13.2 g) in the course of 30 minutes and the mixture was stirred for 1 hour and 40 minutes under ice-cooling. After ammonium chloride (47.2 g) was added to the reaction mixture and stirred for 20 minutes, ice-water (1 liter) was added to the resultant mixture with stirring and allowed to stand to give crystals, which were separated by filtration, washed with water and dried overnight at ambient temperature. The resultant crude crystals were dissolved in chloroform (1.5 liters) under heating. Insoluble materials were filtered off and the filtrate was concentrated under reduced pressure to give crystals, which were dissolved in methanol (300 ml) under heating and allowed to stand at ambient temperature. The resultant crystals were separated by filtration, washed with methanol and dried under reduced pressure to give yellowish crystalline diethyl [(6-nitro-4-quinazolinylamino)methylene]propanedioate (64.9 g).

mp: 228°–230° C.

IR (Nujol) νmax: 1715, 1640, 1618 cm$^{-1}$

N.M.R. δppm (CDCl$_3$): 1.40 (3H, t, J=7.0 Hz), 1.46 (3H, t, J=7.0 Hz), 4.33 (2H, q, J=7.0 Hz), 4.46 (2H, q, J=7.0 Hz), 8.18 (1H, d, J=9.0 Hz), 8.7 (1H, dd, J=2.0 and 9.0 Hz), 8.98 (1H, d, J=2.0 Hz), 9.06 (1H, s), 9.3 (1H, d, J=12.0 Hz), 12.55 (1H, d, J=12.0 Hz)

EXAMPLE 11

A mixture of 4-amino-6-chloroquinazoline (8.7 g) and diethyl ethoxymethylenepropanedioate (11.53 g) in N,N-dimethylformamide (25 ml) was stirred for 2 hours and 40 minutes at 150° C. After the reaction mixture was cooled to ambient temperature, to the mixture was added water with stirring to give crystals, which were washed with water, dried under reduced pressure and dissolved in ethyl acetate under heating. Insoluble materials were filtered off. To the filtrate was added hexane and allowed to stand at ambient temperature to give crystals, which were separated by filtration and washed with a mixture of ethyl acetate and hexane to give a mixture (13.48 g) of crystalline diethyl [(6-chloro-4-quinazolinylamino)methylene]propanedioate and ethyl 10-chloro-4-oxo-4H-pyrimido[1,2-c]quinazoline-3-carboxylate.

(a) Diethyl [(6-chloro-4-quinazolinylamino)methylene]propanedioate

N.M.R. $\delta$ppm (CDCl$_3$): 1.3–1.6 (6H, m), 4.2–4.6 (4H, m), 7.7–8.2 (3H, m), 8.9 (1H, s), 9.26 (1H, d, J=11.0 Hz), 12.16 (1H, broad d, J=11.0 Hz)

(b) Ethyl 10-chloro-4-oxo-4H-pyrimido[1,2-c]-quinazoline-3-carboxylate

N.M.R. $\delta$ppm (CDCl$_3$): 1.43 (3H, t, J=7.0 Hz), 4.40 (2H, q, J=7.0 Hz), 7.88 (2H, broad s), 8.70 (1H, m), 8.93 (1H, s), 9.54 (1H, s)

EXAMPLE 12

A mixture of 4-amino-7-chloroquinazoline (1.3 g) and diethyl ethoxymethylenepropanedioate (1.72 g) in N,N-dimethylformamide (6 ml) was stirred for 2 hours at 150° C. The resultant mixture was cooled to ambient temperature and poured into ice-water to give crystals, which were separated by filtration, washed with water and recrystallized from ethanol to give a mixture (1.65 g) of diethyl [(7-chloro-4-quinazolinylamino)methylene]propanedioate and ethyl 9-chloro-4-oxo-4H-pyrimido[1,2-c]quinazoline-3-carboxylate. The mixture was subjected to a column chromatography using silica gel (developing solvent: a mixture of benzene and ethyl acetate (10:1)) to give purified crystals.

(a) Diethyl [(7-chloro-4-quinazolinylamino)methylene]propanedioate

N.M.R. $\delta$ppm (CDCl$_3$): 1.42 (6H, m), 4.35 (4H, m), 7.56 (1H, dd, J=2.0 and 8.0 Hz), 7.90 (1H, d, J=8.0 Hz), 7.97 (1H, broad s), 8.90 (1H, s), 9.27 (1H, d, J=12.0 Hz), 12.26 (1H, d, J=12.0 Hz)

(b) Ethyl 9-chloro-4-oxo-4H-pyrimido[1,2-c]quinazoline-3-carboxylate

N.M.R. $\delta$ppm (CDCl$_3$): 1.43 (3H, t, J=7.5 Hz), 4.46 (2H, q, J=7.5 Hz), 7.72 (1H, dd, J=2.0 and 9.0 Hz), 8.02 (1H, d, J=2 Hz), 8.80 (1H, d, J=9.0 Hz), 9.03 (1H, s), 9.66 (1H, s)

EXAMPLE 13

A mixture of 4-aminoquinazoline (7.27 g) and dimethyl methoxymethylenepropanedioate (9.6 g) in N,N-dimethylformamide (35 ml) was stirred for 2 hours at 150° C. The reaction mixture was cooled to ambient temperature and poured into ice-water to give crystals, which were separated by filtration, washed with water and dried to ambient temperature to give a mixture (13.3 g) of dimethyl [(4-quinazolinylamino)methylene]propanedioate and methyl 4-oxo-4H-pyrimido[1,2-c]quinazoline-3-carboxylate.

(a) Dimethyl [(4-quinazolinylamino)methylene]propanedioate

N.M.R. $\delta$ppm (CDCl$_3$): 3.87 (6H, s), 7.5–8.2 (4H, m), 9.07 (1H, s), 9.37 (1H, d, J=12.0 Hz), 12.3 (1H, d, J=12.0 Hz)

(b) Methyl 4-oxo-4H-pyrimido[1,2-c]quinazoline-3-carboxylate

N.M.R. $\delta$ppm (CDCl$_3$): 4.03 (3H, s), 7.6–8.12 (3H, m), 8.88 (1H, d, J=8.0 Hz), 9.10 (1H, s), 9.73 (1H, s)

EXAMPLE 14

(a) A mixture of 4-amino-6,7-dimethylquinazoline (11.3 g) and diethyl ethoxymethylenepropanedioate (15.55 g) in N,N-dimethylformamide (45 ml) was stirred for 4 hours at 110° C. After the reaction mixture was cooled to ambient temperature, to the mixture was added water to give crystals, which were separated by filtration, washed with water and dried under reduced pressure to give crude crystals (18.5 g). The crude crustals were dissolved in 1% methanol-chloroform solution (500 ml) and concentrated under reduced pressure after insoluble materials were removed by filtration. The residue was recrystallized from chloroform to give crystalline ethyl 9,10-dimethyl-4-oxo-4H-pyrimido[1,2-c]quinazoline-3-carboxylate (3.57 g).

mp: 221°–223° C.

IR (Nujol) $\nu$max: 1710, 1690, 1610, 810 cm$^{-1}$

N.M.R. $\delta$ppm (CDCl$_3$): 1.4 (3H, t, J=7.0 Hz), 2.5 (6H, s), 4.34 (2H, quartet, J=7.0 Hz), 7.8 (1H, s), 8.6 (1H, s), 9.7 (1H, s), 11.35 (1H, s)

(b) A mixture of ethyl 9,10-dimethyl-4-oxo-4H-primido[1,2-c]quinazoline-3-carboxylate (4.46 g) and anhydrous dimethylsulfoxide (17 ml) was stirred at ambient temperature. To the mixture was dropwise 1 N sodium-ethoxide-ethanol solution (20 ml) and the reaction mixture was stirred for 3 hours at ambient temperature. To the resultant mixture was added ammonium chloride (2.45 g) and the mixture was stirred for 5 minutes. To the mixture was added water and extracted twice with chloroform. After washing three times with water and with aqueous solution saturated with sodium chloride, the combined chloroform layer was treated with activated charcoal, dried over magnesium sulfate and concentrated under reduced pressure to give a residue, which was dissolved in a mixture of chloroform and ethyl acetate. Insoluble materials were removed by filtration. The filtrate was concentrated under reduced pressure and recrystallized twice from ethyl acetate and from a mixture of chloroform and hexane to give diethyl [(6,7-dimethyl-4-quinazolinylamino)methylene]propanedioate (2.01 g).

mp: 146°–148° C.

IR (Nujol) $\nu$max: 3160, 1730, 1690, 1655, 1625, 1615 cm$^{-1}$

N.M.R. $\delta$ppm (CDCl$_3$): 1.32 (3H, t, J=7.0 Hz), 1.4 (3H, t, J=7.0 Hz), 2.5 (6H, s), 4.3 (2H, q, J=7.0 Hz), 4.43 (2H, q, J=7.0 Hz), 7.66 (1H, s), 7.76 (1H, s), 8.9 (1H, s), 9.36 (1H, d, J=12.0 Hz), 11.56 (1H, d, J=12.0 Hz)

EXAMPLE 15

A suspension of diethyl [(6-nitro-4-quinazolinylamino)methylene]propanedioate (2.8 g) in N,N-dimethylformamide (152 ml) was shaken with 10% palladium on carbon (0.93 g) in hydrogen atmosphere at ambient temperature for an hour. After the reaction was completed, the catalyst was removed by filtration and washed with chloroform. The combined filtrate and washing was concentrated under reduced pressure to give a residue, to which was added toluene and concentrated under reduced pressure. This operation was repeated to give crystalline diethyl [(6-amino-4-quinazolinylamino)methylene]propanedioate (2.50 g).

IR (Nujol) $\nu$max: 3260, 1690, 1640, 1630, 1600 cm$^{-1}$

N.M.R. $\delta$ppm (DMSO-d$_6$): 1.3 (3H, t, J=7.0 Hz), 1.35 (3H, t, J=7 Hz), 4.23 (2H, quartet, J=7.0 Hz), 4.39 (2H, quartet, J=7.0 Hz), 7.2 (1H, d, J=2.0 Hz), 7.4 (1H, dd, J=2 and 10 Hz), 7.83 (1H, d, J=10.0 Hz), 9.36 (1H, s), 9.5-10 (3H, m), 12.3 (1H, d, J=14.0 Hz)

EXAMPLE 16

A mixture of diethyl [(6-amino-4-quinazolinylamino)methylene]propanedioate (2.5 g), pyridine (1.2 g) and dichloromethane (55 ml) was stirred under ice-cooling. To the reaction mixture was added dropwise isobutyryl chloride (1.06 g). The reaction mixture was stirred under ice-cooling for 30 minutes and at ambient temperature for 20 minutes. After ice-water was added to the reaction mixture, the resultant mixture was stirred and extracted with chloroform. Insoluble materials were removed by filtration from the extracts. The extracts were washed three times with water and with aqueous solution saturated with sodium chloride, dried over magnesium sulfate and concentrated under reduced pressure. The resultant residue was purified by a column chromatography using silica gel (developing solvent: chloroform) and crystallized from a mixture of chloroform and hexane to give crystalline diethyl [(6-isobutyramido-4-quinazolinylamino)methylene]propanedioate (1.28 g). Crystals (0.67 g) of the same compound were recovered from the mother liquor by substantially the same crystallization as mentioned above.

mp: 190°-193° C.

IR (Nujol) $\nu$max: 3530, 1775, 1710, 1700, 1678, 1660, 1615 cm$^{-1}$

N.M.R. $\delta$ppm (CDCl$_3$): 1.2-1.5 (12H, m), 2.2-2.8 (1H, m), 4.25 (2H, quartet, J=6 Hz), 4.39 (2H, quartet, J=6 Hz), 7.4-8.2 (4H, m), 8.8 (1H, s), 9.15 (1H, d, J=12 Hz), 12.06 (1H, d, J=12 Hz)

EXAMPLE 17

The following compounds were prepared in substantially the same manner as that of Example 16.

(1) Diethyl [(6-acetamido-4-quinazolinylamino)methylene]propanedioate mp: 178°-180° C. (recrystallized from a mixture of tetrahydrofuran and hexane)

IR (Nujol) $\nu$max: 3380, 1695, 1660, 1630, 1610 cm$^{-1}$

N.M.R. $\delta$ppm (CDCl$_3$): 1.32 (3H, t, J=6 Hz), 1.36 (3H, t, J=6 Hz), 2.08 (3H, s), 4.3 (4H, quartet, J=6 Hz), 7.7-8.1 (2H, m), 8.44 (1H, s), 8.83 (1H, s), 9.28 (1H, s), 9.28 (1H, d, J=12 Hz), 11.98 (1H, d, J=12 Hz)

(2) Diethyl [(6-propionamido-4-quinazolinylamino)methylene]propanedioate mp: 190°-193° C. (recrystallized from a mixture of ethyl acetate and hexane)

IR (Nujol) $\nu$max: 3340, 1736, 1670, 1660, 1635, 1572 cm$^{-1}$

N.M.R. $\delta$ppm (CDCl$_3$): 1.2-1.6 (9H, m), 2.50 (2H, quartet, J=7.0 Hz), 4.34 (2H, quartet, J=7.0 Hz), 4.40 (2H, quartet, J=7.0 Hz), 8.0 (2H, m), 8.40 (1H, broad s), 8.56 (1H, s), 8.90 (1H, s), 9.36 (1H, d, J=12 Hz), 12.1 (1H, d, J=12 Hz)

(3) Diethyl [(6-butyramido-4-quinazolinylamino)methylene]propanedioate mp: 187°-190° C. (recrystallized from methanol)

IR (Nujol) $\nu$max: 3380, 1748, 1680, 1625, 1580, 1554 cm$^{-1}$

N.M.R. $\delta$ppm (CDCl$_3$): 0.98 (3H, t, J=7.0 Hz), 1.27 (3H, t, J=6.8 Hz), 1.33 (3H, t, J=6.8 Hz), 1.80 (2H, m), 2.43 (2H, t, J=7 Hz), 4.33 (4H, m), 8.0 (2H, m), 8.43 (1H, broad s), 8.90 (2H, s), 9.40 (1H, d, J=12 Hz), 12.1 (1H, d, J=12 Hz)

(4) Diethyl [(6-hexanamido-4-quinazolinylamino)methylene]propanedioate mp: 157°-162° C.(recrystallized from chloroform, ethylacetate and hexane)

IR (Nujol) $\nu$max: 1686, 1640, 1620, 1600, 1550 cm$^{-1}$

N.M.R. $\delta$ppm (CDCl$_3$): 0.6-1.2 (3H, m), 1.2-2.2 (12H, m), 2.80 (2H, broad t, J=7.0 Hz), 4.36 (4H, m), 7.83 (1H, d, J=9.0 Hz), 8.1-8.5 (2H, m), 8.76 (1H, s), 9.16 (1H, d, J=12 Hz), 10.2 (1H, s), 12.3 (1H, d, J=12 Hz)

(5) Diethyl [(6-ethoxalamido-4-quinazolinylamino)methylene]propanedioate mp: 191°-192° C. (recrystallized from chloroform, ethylacetate and hexane)

IR (Nujol) $\nu$max: 3300, 1720, 1685, 1650, 1630, 1610 cm$^{-1}$

N.M.R. $\delta$ppm (CDCl$_3$): 1.27-1.66 (9H, m), 4.17-4.66 (6H, m), 7.9-8.27 (2H, m), 8.50 (1H, broad s), 8.93 (1H, s), 9.33 (1H, d, J=12.0 Hz), 9.43 (1H, s), 12.23 (1H, d, J=12.0 Hz)

(6) Diethyl [(6-cyclohexanamido-4-quinazolinylamino)methylene]propanedioate mp: 202°-208° C. (recrystallized from a mixture of chloroform and methanol)

IR (Nujol) $\nu$max: 3340, 1728, 1660, 1634, 1615, 1570 cm$^{-1}$

N.M.R. $\delta$ppm (CDCl$_3$): 1.37 (6H, t, J=7.0 Hz), 1.0-2.6 (11H, m), 4.37 (4H, m), 7.8-8.2 (3H, m), 8.33 (1H, broad s), 8.90 (1H, s), 9.37 (1H, d, J=12.0 Hz), 12.1 (1H, d, J=12.0 Hz)

(7) Diethyl [(6-benzamido-4-quinazolinylamino)methylene]propanedioate mp: 164°-165° C. (recrystallized from a mixture of chloroform and hexane)

IR (Nujol) $\nu$max: 3400, 1715, 1710, 1660, 1640, 1610 cm$^{-1}$

N.M.R. $\delta$ppm (CDCl$_3$): 1.33 (6H, t, J=8.0 Hz), 4.30 (2H, quartet, J=8.0 Hz), 4.33 (2H, quartet, J=8.0 Hz), 7.4-8.3 (7H, m), 8.46 (1H, s), 8.7 (1H, s), 8.90 (1H, s), 9.33 (1H, d, J=12 Hz), 12.1 (1H, d, J=12 Hz)

(8) Diethyl [(6-phenylacetamido-4-quinazolinylamino)methylene]propanedioate mp: 113°-117° C. (recrystallized from a mixture of ether and hexane)

IR (Nujol) $\nu$max: 3600, 1748, 1710, 1690, 1660, 1632, 1620 cm$^{-1}$

N.M.R. $\delta$ppm (CDCl$_3$): 1.33 (3H, t, J=7.0 Hz), 1.37 (3H, t, J=7.0 Hz), 3.80 (2H, s), 4.33 (4H, m), 7.33 (5H, s), 7.83 (2H, broad s), 8.43 (2H, broad s), 8.83 (1H, s), 9.33 (1H, d, J=12 Hz), 12.0 (1H, d, J=12 Hz)

(9) Diethyl [(6-pivalamido-4-quinazolinylamino)methylene]propanedioate mp: 141°-142° C. (recrystallized from a mixture of ether and ethyl acetate IR (Nujol) $\nu$max: 3380, 1720, 1672, 1652, 1628, 1610 cm$^{-1}$ N.M.R. $\delta$ppm (CDCl$_3$): 1.2-1.7 (15H, m), 4.2-4.7 (4H, m), 7.7-8.16 (3H, m), 8.33 (1H, s), 8.83 (1H, s), 9.33 (1H, d, J=12 Hz), 12.0 (1H, d, J=12 Hz)

EXAMPLE 18

A mixture of diethyl [(6-amino-4-quinazolinylamino)methylene]propanedioate (3.03 g), pyridine (3.63 g) and dichloromethane (93 ml) was ice-cooled. To the mixture was added acetic anhydride (1.88 g). The reaction mixture was stirred for 30 minutes under ice-cooling and then for 2 hours and 15 minutes at ambient temperature. Ice water was added to the mixture. The resultant mixture was extracted with chloroform. The organic layer was washed three times with water and with aqueous solution saturated with sodium chloride, dried over anhydrous magnesium sulfate and concentrated under reduced pressure to give a residue, which was purified by a column chromatography on silica gel (developing solvent: chloroform) and recrystallized from chloroform, ethyl acetate and hexane to give crystalline diethyl [(6-acetamido-4-quinazolinylamino)methylene]-propanedioate (2.2 g).

N.M.R. δppm (CDCl$_3$): 1.32 (3H, t, J=6 Hz), 1.36 (3H, t, J=6 Hz), 2.08 (3H, s), 4.3 (4H, quartet, J=6 Hz), 7.7-8.1 (2H, m), 8.44 (1H, s), 8.83 (1H, s), 9.28 (1H, s), 9.28 (1H, d, J=12 Hz), 11.98 (1H, d, J=12 Hz)

EXAMPLE 19

A suspension of diethyl [(6-nitro-4-quinazolinylamino)methylene]propanedioate (0.7 g) in N,N-dimethylformamide (56 ml) was shaken with 10% palladium on carbon (60 mg) in hydrogen atmosphere at ambient temperature until hydrogen gas (160 ml) was absorbed. The catalyst was removed by filtration and washed with a small volume of chloroform. To the combined filtrate and washings was added a mixture of acetic anhydride (15 ml) and pyridine (15 ml) and the reaction mixture was allowed at ambient temperature for 1 day. The reaction mixture was concentrated under reduced pressure to give a residue, to which was added toluene and the mixture was concentrated under reduced pressure. This operation was repeated twice to remove N,N-dimethylformamide and acetic anhydride. The resultant residue was subjected to fractionation on silica gel column (developing solvent: ethyl acetate and chloroform) to give crude crystals of diethyl [(6-N,N-diacetylamino-4-quinazolinylamino)methylene]-propanedioate (0.24 g). The crude crystals were recrystallized from a mixture of ethyl acetate and hexane to give purified crystals of the same compound.

mp: 148°-151° C.

IR (Nujol) νmax: 1800, 1700, 1645, 1608 cm$^{-1}$

N.M.R. δppm (CDCl$_3$): 1.24-1.52 (6H, m), 2.24 (3H, s), 2.40 (3H, s), 4.22-4.55 (4H, m), 7.92 (1H, d, J=2.0 Hz), 7.98 (1H, d, J=9.0 Hz), 8.16 (1H, dd, J=2.0 and 9.0 Hz), 8.92 (1H, s), 9.3 (1H, d, J=12.0 Hz), 12.24 (1H, broad d, J=12 Hz)

EXAMPLE 20

A suspension of diethyl [(6-nitro-4-quinazolinylamino)methylene]propanedioate (10.8 g) in N,N-dimethylformamide (380 ml) was shaken with 10% palladium on carbon (3.6 g) in hydrogen atmosphere at ambient temperature until hydrogen gas (2030 ml) was absorbed. The catalyst was removed by filtration and washed with a small volume of N,N-dimethylformamide. To the combined filtrate and washings was added pyridine (17 ml) and the mixture was cooled over an ice-bath. To the solution was added dropwise pivalic chloride (6.33 g) for 20 minutes and then the reaction mixture was stirred for 2 hours and 40 minutes at ambient temperature. To the resultant mixture was added ice-water under stirring and then the mixture was concentrated under reduced pressure. To the residue was added chloroform and then the mixture was washed with an aqueous solution saturated with sodium bicarbonate and with water. Insoluble materials were removed by filtration from the chloroform layer. The filtrate was washed with aqueous solution saturated with sodium chloride, dried over anhydrous magnesium sulfate and concentrated under reduced pressure. The resultant oil was subjected to a chromatography using silica gel (developing solvent: dichloromethane) to give the first Fraction A and the second Fraction B. The Fraction A was concentrated under reduced pressure to give crystalline diethyl [(6-pivalamido-4-quinazolinylamino)methylene]propanedioate (4.6 g). Further, Fraction B was concentrated under reduced pressure to give a solid (3.6 g), which was suspended in methanol. Insoluble materials were separated by filtration and recrystallized from ethyl acetate to give crystalline diethyl [(6-formamido-4-quinazolinylamino)methylene]propanedioate (0.58 g).

mp: 182°-185° C.

EXAMPLE 21

To diethyl [(4-quinazolinylamino)methylene]propanedioate (16.0 g) was added diphenylether (70 ml) which had been heated at 250° C. in advance. The reaction mixture was stirred at 250°-260° C. for 20 minutes and cooled to ambient temperature. To the resultant mixture was added hexane. The mixture was stirred to give crystals, which was washed with hexane and dried. The crude crystals were dissolved in ethyl acetate under heating. After insoluble materials were removed by filtration, the filtrate was concentrated under reduced pressure to a volume of 200 ml. To the concentrate was added hexane and the mixture was allowed to stand at ambient temperature to precipitate crystals, which were separated by filtration, washed with a mixture of ethyl acetate and hexane and dried to give crystalline ethyl 4-oxo-4H-pyrimido[1,2-c]quinazoline-3-carboxylate (12.4 g).

mp: 171°-172° C.

IR (Nujol) νmax: 1725, 1702, 1620 cm$^{-1}$

N.M.R. δppm (CDCl$_3$): 1.43 (3H, t, J=7.0 Hz), 4.40 (2H, quartet, J=7.0 Hz), 7.6-8.2 (3H, m), 8.84 (1H, broad d, J=7.0 Hz), 9.03 (1H, s), 9.66 (1H, s)

EXAMPLE 22

The following compounds were prepared in substantially the same manner as that of Example 21.

(1) Methyl 4-oxo-4-H-pyrimido[1,2-c]quinazoline-3-carboxylate mp: 203°-205° C. (recrystallized from chloroform)

N.M.R. δppm (CDCl$_3$): 4.03 (3H, s), 7.6-8.12 (3H, m), 8.88 (1H, d, J=8.0 Hz), 9.10 (1H, s), 9.73 (1H, s)

(2) Ethyl 4-oxo-10-chloro-4H-pyrimido[1,2-c]quinazoline-3-carboxylate mp: 161°-163° C. (recrystallized from a mixture of chloroform and hexane) P IR (Nujol) νmax: 1752, 1700, 1621, 1584 cm$^{-1}$ N.M.R. δppm (CDCl$_3$): 1.43 (3H, t, J=7.0 Hz), 4.40 (2H, quartet, J=7.0 Hz), 7.88 (2H, broad s), 8.70 (1H, m), 8.93 (1H, s), 9.54 (1H, s)

(3) Ethyl 4-oxo-9-chloro-4H-pyrimido[1,2-c]quinazoline-3-carboxylate mp: 192.5°-193.5° C. (recrystallized from a mixture of diphenyl ether and hexane)

IR (Nujol) νmax: 1755, 1710, 1610, 1603, 1580 cm$^{-1}$

N.M.R. δppm (CDCl$_3$): 1.43 (3H, t, J=7.5 Hz), 4.46 (2H, quartet, J=7.5 Hz), 7.72 (1H, dd, J=2.0 and 9.0 Hz), 8.02 (1H, d, J=2 Hz), 8.80 (1H, d, J=9.0 Hz), 9.03 (1H, s), 9.66 (1H, s)

(4) Ethyl 4-oxo-10-methyl-4H-pyrimido[1,2-c)quinazoline-3-carboxylate mp: 182°-183° C. (recrystallized from a mixture of chloroform, ethyl acetate and hexane)

IR (Nujol) νmax: 1752, 1690, 1614 cm$^{-1}$

N.M.R. δppm (CDCl$_3$): 1.42 (3H, t, J=7.8 Hz), 2.56 (3H, s), 4.40 (2H, quartet, J=7.8 Hz), 7.76 (2H, m), 8.52 (1H, broad s), 8.92 (1H, s), 9.50 (1H, s)

(5) Ethyl 4-oxo-10-nitro-4H-pyrimido[1,2-c]quinazoline-3-carboxylate mp: 171°–174° C. (recrystallized from a mixture of chloroform and hexane)

IR (Nujol) νmax: 1720, 1700, 1625, 1585 cm$^{-1}$

N.M.R. δppm (CDCl$_3$): 1.43 (3H, t, J=6.0 Hz), 4.36 (2H, quartet, J=6.0 Hz), 8.16 (1H, d, J=9.0 Hz), 8.73 (1H, dd, J=3.0 and 9.0 Hz), 9.03 (1H, s), 9.66 (1H, d, J=3.0 Hz), 9.73 (1H, s)

(6) Ethyl 4-oxo-10-phenoxy-4H-pyrimido[1,2-c]quinazoline-3-carboxylate mp: 210°–213° C. (recrystallized from a mixture of chloroform, ethyl acetate and hexane)

IR (Nujol) νmax: 1750, 1680, 1618, 1593 cm$^{-1}$

N.M.R. δppm (CDCl$_3$): 1.43 (3H, t, J=7.0 Hz), 4.43 (2H, d, J=7.0 Hz), 7.0–8.4 (7H, m), 8.0 (1H, d, J=8.0 Hz), 9.0 (1H, s), 9.63 (1H, s)

(7) Ethyl 4-oxo-10-(dimethylamino)-4H-pyrimido[1,2-c]-quinazoline-3-carboxylate mp: 240°–242° C. (recrystallized from tetrahydrofuran)

IR (Nujol) νmax: 1745, 1685, 1612, 1595 cm$^{-1}$

N.M.R. δppm (CDCl$_3$): 1.44 (3H, t, J=7.5 Hz), 3.16 (6H, s), 4.44 (2H, quartet, J=7.5 Hz), 7.3–7.5 (2H, m), 7.80 (1H, m), 8.98 (1H, s), 9.44 (1H, s)

(8) Ethyl 4-oxo-10-ethylthio-4H-pyrimido[1,2-c]-quinazoline-3-carboxylate mp: 168°–170° C. (recrystallized from a mixture of chloroform and hexane)

IR (Nujol) νmax: 1750, 1695, 1610, 1495 cm$^{-1}$

N.M.R. δppm (CDCl$_3$): 1.45 (6H, t, J=8.0 Hz), 3.16 (2H, quartet, J=8.0 Hz), 4.47 (2H, quartet, J=8.0 Hz), 7.8–8.0 (2H, m), 8.6 (1H, m), 9.03 (1H, s), 9.60 (1H, s)

(9) Ethyl 4-oxo-9-methoxy-4H-pyrimido[1,2-c]quinazoline-3-carboxylate mp: 202°–206° C. (recrystallized from a mixture of chloroform and hexane)

IR (Nujol) νmax: 1740, 1680, 1615, 1585 cm$^{-1}$

N.M.R. δppm (CDCl$_3$): 1.43 (3H, t, J=7.0 Hz), 4.00 (3H, s), 4.43 (2H, quartet, J=7.0 Hz), 7.40 (2H, m), 8.77 (1H, d, J=10.0 Hz), 9.00 (1H, s), 9.67 (1H, s)

(10) Ethyl 4-oxo-10-acetamido-4H-pyrimido[1,2-c]-quinazoline-3-carboxylate mp: 294°–295° C. (recrystallized from N,N-dimethylformamide)

IR (Nujol) νmax: 3360, 1740, 1720, 1675, 1615 cm$^{-1}$

N.M.R. δppm (DMSO-d$_6$): 1.3 (3H, t, J=6.0 Hz), 2.1 (3H, s), 4.30 (2H, quartet, J=6.0 Hz), 7.83 (1H, d, J=9.0 Hz), 8.1 (1H, dd, J=2.0 and 9.0 Hz), 8.87 (1H, s), 9.03 (1H, d, J=2.0 Hz), 9.36 (1H, s), 10.46 (1H, s)

(11) Ethyl 4-oxo-9-acetamido-4H-pyrimido[1,2-c]quinazoline-3-carboxylate mp: 281°–285° C. (recrystallized from a mixture of N,N-dimethylformamide and water)

IR (Nujol) νmax: 3560, 3400, 1742, 1616, 1588 cm$^{-1}$

(12) Ethyl 4-oxo-10-propionamido-4H-pyrimido[1,2-c]-quinazoline-3-carboxylate mp: 274°–276° C. (recrystallized from a mixture of chloroform and methanol)

IR (Nujol) νmax: 3360, 1740, 1720, 1670, 1618 cm$^{-1}$

N.M.R. δppm (DMSO-d$_6$): 1.13 (3H, t, J=7.0 Hz), 1.30 (3H, t, J=7.0 Hz), 2.43 (2H, quartet, J=7.0 Hz), 4.30 (2H, quartet, J=7.0 Hz), 7.90 (1H, d, J=10.0 Hz), 8.16 (1H, dd, J=2.0 and 10.0 Hz), 8.90 (1H, s), 9.10 (1H, d, J=2.0 Hz), 9.40 (1H, s), 10.43 (1H, s)

(13) Ethyl 4-oxo-10-butyramido-4H-pyrimido[1,2-c]quinazoline-3-carboxylate mp: 278°–282° C. (recrystallized from a mixture of chloroform and methanol)

IR (Nujol) νmax: 3410, 1745, 1712, 1680, 1615 cm$^{-1}$

N.M.R. δppm (CDCl$_3$): 1.03 (3H, t, J=7.0 Hz), 1.43 (3H, t, J=7.0 Hz), 1.76 (2H, m), 2.46 (2H, t, J=7.0 Hz), 4.46 (2H, quartet, J=7.0 Hz), 8.0 (1H, d, J=9.0 Hz), 8.43 (1H, dd, J=2.0 and 9.0 Hz), 8.97 (1H, d, J=2.0 Hz), 9.05 (1H, s), 9.63 (1H, s)

(14) Ethyl 4-oxo-10-isobutyramido-4H-pyrimido[1,2-c]-quinazoline-3-carboxylate P mp: 245°–247° C. (recrystallized from a mixture of chloroform and hexane)

IR (Nujol) νmax: 3400, 1730, 1710, 1690, 1625, 1410 cm$^{-1}$

N.M.R. δppm (DMSO-d$_6$): 1.2–1.8 (9H, m), 2.3–2.9 (1H, m), 4.46 (2H, quartet, J=7.0 Hz), 7.8–8.1 (2H, m), 8.43 (1H, dd, J=2 and 10 Hz), 8.92 (1H, d, J=2 Hz), 9.05 (1H, s), 9.63 (1H, s)

(15) Ethyl 4-oxo-10-hexanamido-4H-pyrimido[1,2-c]-quinazoline-3-carboxylate mp: 231°–234° C. (recrystallized from a mixture of chloroform and methanol)

IR (Nujol) νmax: 3400, 3100, 1745, 1720, 1680, 1610 cm$^{-1}$

N.M.R. δppm (DMSO$_4$-d$_6$): 0.6–2.0 (10H, m), 2.1–2.6 (4H, m), 4.30 (2H, quartet, J=7.0 Hz), 7.9 (1H, d, J=9.0 Hz), 8.16 (1H, dd, J=2.0 and 9.0 Hz), 8.90 (1H, s), 9.13 (1H, d, J=2.0 Hz), 9.40 (1H, s), 10.55 (1H, s)

(16) Ethyl 4-oxo-10-ethoxalamido-4H-pyrimido[1,2-c]-quinazoline-3-carboxylate mp: 263°–264° C. (recrystallized from a mixture of chloroform and methanol)

IR (Nujol) νmax: 3400, 1745, 1725, 1610 cm$^{-1}$

N.M.R. δppm (DMSO-d$_6$): 1.26 (3H, t, J=6 Hz), 1.30 (3H, t, J=6 Hz), 4.3 (2H, quartet, J=6 Hz), 4.36 (2H, quartet, J=6 Hz), 7.96 (1H, d, J=9.0 Hz), 8.33 (1H, dd, J=2 and 9 Hz), 8.9 (1H, s), 9.27 (1H, d, J=2 Hz), 9.43 (1H, s), 11.4 (1H, s)

(17) Ethyl 4-oxo-10-cyclohexanecarboxamido-4H-pyrimido[1,2-c]quinazoline-3-carboxylate mp: 262°–266° C. (recrystallized from a mixture of chloroform and hexane)

IR (Nujol): νmax: 3400, 3100, 1730, 1692, 1672, 1612 cm$^{-1}$

N.M.R. δppm (CDCl$_3$): 1.40 (3H, t, J=7.0 Hz), 1.0–2.6 (11H, m), 4.46 (2H, quartet, J=7.0 Hz), 7.90 (1H, s), 8.0 (1H, d, J=9.0 Hz), 8.43 (1H, dd, J=3.0 and 9.0 Hz), 8.93 (1H, d, J=3.0 Hz), 9.1 (1H, s), 9.66 (1H, s)

(18) Ethyl 4-oxo-10-benazamido-4H-pyrimido[1,2-c]quinazoline-3-carboxylate mp: 237°–239° C. (recrystallized from a mixture of chloroform and methanol)

IR (Nujol) νmax: 3400, 1730, 1680, 1620 cm$^{-1}$

N.M. R. δppm (DMSO-d$_6$): 1.40 (3H, t, J=7.0 Hz), 4.40 (2H, quartet, J=7.0 Hz), 7.5–8.3 (6H, m), 8.55 (1H, dd, J=2.0 and 10.0 Hz), 9.0 (1H, s), 9.40 (1H, d, J=2.0 Hz), 9.53 (1H, s), 10.86 (1H, s)

(19) Ethyl 4-oxo-10-phenylacetamido-4H-pyrimido[1,2-c]quinazoline-3-carboxylate mp: 230°–235° C. (recrystallized from a mixture of methanol and chloroform)

IR (Nujol) νmax: 3370, 1735, 1720, 1670, 1618 cm$^{-1}$

N.M.R. δppm (DMSO-d$_6$): 1.3 (3H, t, J=7.0 Hz), 3.75 (2H, s), 4.33 (2H, quartet, J=7.0 Hz), 7.33 (5H, s), 7.8–8.3 (2H, m), 8.90 (1H, s), 9.12 (1H, d, J=2 Hz), 9.40 (1H, s), 10.76 (1H, s)

(20) Ethyl 4-oxo-10-ethyl-pyrimido[1,2-c]quinazoline-3-carboxylate mp: 168°–170° C. (recrystallized from a mixture of ethyl acetate and hexane)

IR (Nujol) νmax: 1720, 1700, 1620, 1500 cm$^{-1}$

N.M.R. δppm (CDCl₃): 1.4 (3H, t, J=8.0 Hz), 1.46 (3H, t, J=8.0 Hz), 2.95 (2H, quartet, J=8.0 Hz), 4.46 (2H, quartet, J=8.0 Hz), 7.9–8.1 (2H, m), 8.7 (1H, s), 9.06 (1H, s), 9.66 (1H, s)

(21) Ethyl 4-oxo-10-butyl-pyrimido[1,2-c]quinazoline-3-carboxylate mp: 151°–154° C. (recrystallized from a mixture of ethyl acetate and hexane)

IR (Nujol) νmax: 1720, 1690, 1610, 1490, 800 cm⁻¹

N.M.R. δppm (CCl₄): 0.8–2.1 (10H, m), 2.9 (2H, t, J=8.0 Hz), 4.43 (2H, quartet, J=7.0 Hz), 7.7–8.0 (2H, m), 8.63 (1H, s), 8.9 (1H, s), 9.53 (1H, s)

(22) Ethyl 4-oxo-8-methyl-4H-pyrimido[1,2-c]quinazoline-3-carboxylate mp: 166°–172° C. (recrystallized from a mixture of chlororform, ethyl acetate and hexane)

IR (Nujol) νmax: 1750, 1692, 1622, 1600 cm⁻¹

N.M.R. δppm (CDCl₃): 1.46 (3H, t, J=7.0 Hz), 2.73 (3H, s), 4.46 (2H, quartet, J=7.0 Hz), 7.4–7.9 (2H, m), 8.60 (1H, broad d, J=8.0 Hz), 8.93 (1H, s), 9.56 (1H, s)

(23) Ethyl 4-oxo-10-propyl-4H-pyrimido[1,2-c]quinazoline-3-carboxylate mp: 161°–163° C. (recrystallized from benzene)

IR (Nujol): νmax: 1700, 1620, 1610, 1500, 1150 cm⁻¹

N.M.R. δppm (CDCl₃): 1.0 (3H, t, J=7.0 Hz), 1.3–2.2 (5H, m), 2.9 (2H, t, J=7.0 Hz), 4.43 (2H, quartet, J=7.0 Hz), 7.8–8.1 (2H, m), 8.63 (1H, s), 9.0 (1H, s), 9.6 (1H, s)

(24) Ethyl 4-oxo-9-methyl-4H-pyrimido[1,2-c]quinazoline-3-carboxylate mp: 186°–188° C. (recrystallized from tetrahydrofuran)

IR (Nujol) νmax: 1705, 1680, 1490, 1300, 800 cm⁻¹

N.M.R. δppm (CDCl₃): 1.4 (3H, t, J=8.0 Hz), 2.6 (3H, s), 4.33 (2H, quartet, J=8.0 Hz), 7.56 (1H, d, J=8.0 Hz), 7.76 (1H, s), 8.7 (1H, d, J=8.0 Hz), 9.0 (1H, s), 9.63 (1H, s)

(25) Ethyl 4-oxo-10-(4-methylpiperazinyl)-4H-pyrimido[1,2-c]quinazoline-3-carboxylate mp: 203°–206° C. (recrystallized from a mixture of ethanol and chloroform)

IR (Nujol) νmax: 1740, 1680, 1608 cm⁻¹

N.M.R. δppm (CDCl₃): 1.43 (3H, t, J=7.0 Hz), 2.36 (3H, s), 2.60 (4H, m), 3.46 (4H, m), 4.43 (2H, quartet, J=7.0 Hz), 7.50 (1H, dd, J=3.0 and 8.5 Hz), 7.80 (1H, d, J=8.5 Hz), 8.03 (1H, d, J=3.0 Hz), 8.96 (1H, s), 9.46 (1H, s)

(26) Ethyl 4-oxo-9,10-dimethoxy-4H-pyrimido[1,2-c]quinazoline-3-carboxylate mp: 262°–264° C. (recrystallized from chloroform)

IR (Nujol) νmax: 1705, 1675, 1595 cm⁻¹

N.M.R. δppm (CDCl₃): 1.43 (3H, t, J=7.0 Hz), 4.13 (6H, s), 4.46 (2H, quartet, J=7.0 Hz), 7.40 (1H, s), 8.16 (1H, s), 9.05 (1H, s), 9.67 (1H, s)

(27) Ethyl 4-oxo-10-pivalamido-4H-pyrimido[1,2-c]quinazoline-3-carboxylate mp: 247°–250° C. (recrystallized from a mixture of chloroform and methanol)

IR (Nujol) νmax: 3370, 1712, 1672, 1610 cm⁻¹

N.M.R. δppm (CDCl₃): 1.45 (3H, t, J=7.0 Hz), 1.37 (9H, s), 4.46 (2H, quartet, J=7.0 Hz), 7.96 (1H, d, J=9.5 Hz), 8.41 (1H, dd, J=3 and 9.5 Hz), 9.13 (2H, broad s), 9.63 (1H, s), 12.1 (1H, s)

(28) Ethyl 4-oxo-6-hydroxy-4H-pyrimido[1,2-c]quinazoline-3-carboxylate mp: >270° C. (recrystallized from a mixture of chloroform and methanol)

IR (Nujol) νmax: 1770, 1742, 1705, 1638, 1615, 1602 cm⁻¹

N.M.R. δppm (DMSO-d₆): 1.32 (3H, t, J=6.0 Hz), 4.30 (2H, quartet, J=6.0 Hz), 7.2–7.6 (2H, m), 7.74 (1H, t, J=8.0 Hz), 8.26 (1H, d, J=8.0 Hz), 8.92 (1H, s), 12.5 (1H, broad s)

(29) Ethyl 4-oxo-6-methyl-4H-pyrimido[1,2-c]quinazoline-3-carboxylate mp: 168° C. (recrystallized from benzene)

IR (Nujol) νmax: 1735, 1700, 1615, 1590 cm⁻¹

N.M.R. δppm (CDCl₃): 1.43 (3H, t, J=7.0 Hz), 3.20 (3H, s), 4.47 (2H, quartet, J=7.0 Hz), 7.6–8.0 (3H, m), 8.73–8.93 (1H, m), 8.93 (1H, s).

(30) Ethyl 4-oxo-6-hydroxy-10-ethyl-4H-pyrimido[1,2-c]-quinazoline-3-carboxylate mp: 315°–318° C. (recrystallized from a mixture of chloroform and methanol)

IR (Nujol) νmax: 1748, 1630, 1595 cm⁻¹

EXAMPLE 23

A mixture of diethyl [(2-allyloxy-4-quinazolinylamino)methylene]propanedioate (6.0 g) in diphenyl ether (14 ml) was stirred for 15 minutes at 260° C. and then cooling to ambient temperature. Hexane was added to the resultant mixture to give precipitates, which separated by filtration and washed with hexane to give crude crystals. The crude crystals were subjected to a column chromatography using silica gel (developing solvent: chloroform) to give the first Fraction A and the second Fraction B.

The fraction A was concentrated under reduced pressure to give crystals, which were recrystallized from a mixture of chloroform, ethyl acetate and hexane to give crystalline ethyl 4-oxo-6-allyloxy-4H-pyrimido-[1,2-c]quinazoline-3-carboxylate (1.8 g).

mp: 191°–195° C.

IR (Nujol) νmax: 1775, 1725, 1690, 1608 cm⁻¹

N.M.R. δppm (CDCl₃): 1.40 (3H, t, J=7.0 Hz), 4.43 (2H, quartet, J=7.0 Hz), 4.90 (2H, m), 5.40 (2H, m), 6.0 (1H, m), 7.30 (2H, m), 7.80 (1H, t, J=7.0 Hz), 8.56 (1H, d, J=7.0 Hz), 8.66 (1H, s)

On the other hand, the Fraction B was concentrated under reduced pressure to give crystals, which were recrystallized from a mixture of ethyl acetate and hexane to give crystalline ethyl 4,6-dioxo-7-allyl-4H-6,7-dihydropyrimido[1,2-c]quinazoline-3-carboxylate (1.5 g).

mp: 163°–166° C.

IR (Nujol) νmax: 1740, 1710, 1682, 1645, 1615, 1600 cm⁻¹

N.M.R. δppm (CDCl₃): 1.40 (3H, t, J=7.0 Hz), 4.40 (2H, quartet, J=7.0 Hz), 4.88 (2H, m), 5.24 (2H, m), 6.92 (1H, m), 7.34 (2H, m), 7.74 (1H, t, J=8.0 Hz), 8.60 (1H, d, J=7.0 Hz), 9.14 (1H, s)

EXAMPLE 24

A mixture of diethyl [(2-methoxy-4-quinazolinylamino)methylene]propanedioate (8.0 g) in diphenylether (30 ml) was stirred for 32 minutes at 260° C. The reaction mixture was allowed to stand overnight at ambient temperature to give crystals, which were separated by filtration and washed with hexane to give crude crystals (A). Further, a large volume of hexane was added to the filtrate and the mixture was allowed to stand overnight at ambient temperature to give crystals, which were recrystallized from a mixture of ethyl acetate and hexane to give crude crystals (B) and mother liquor (A). The crude crystals (A) and (B) were combined and subjected to a column chromatography using silica gel (developing solvent: a mixture of ethyl acetate and chloroform=1:9). One of the fractions was concentrated under reduced pressure to give crystals, which were recrystallized from a mixture of chloroform and hexane to give crystalline ethyl 4,6-dioxo-7-methyl-4H,6H-6,7-dihydropyrimido[1,2-c]quinazoline-3-carboxylate (0.7 g).

mp: 265°–271° C.

IR (Nujol) $\nu$max: 1732, 1642, 1610 cm$^{-1}$

N.M.R. $\delta$ppm (CDCl$_3$): 1.40 (3H, t, J=7.8 Hz), 3.80 (3H, s), 4.45 (2H, quartet, J=7.8 Hz), 7.30–8.00 (3H, m), 8.73 (1H, d, J=8.0 Hz), 9.22 (1H, s)

Further, mother liquor (A) was concentrated under reduced pressure and subjected to a column chromatography using silica gel (developing solvent: chloroform). The eluate was concentrated under reduced pressure to give crystals, which were recrystallized from a mixture of chloroform and hexane to give crystalline ethyl 4-oxo-6-methoxy-4H-pyrimido[1,2-c[quinazoline-3-carboxylate (0.45 g).

mp: 180°–183° C.

IR (Nujol) $\nu$max: 1765, 1708, 1625, 1610, 1590 cm$^{-1}$

N.M.R. $\delta$ppm (CDCl$_3$): 1.46 (3H, t, J=7.0 Hz), 4.33 (3H, s), 4.46 (2H, quartet, J=7.0 Hz), 7.3–8.0 (3H, m), 8.70 (1H, d, J=7.0 Hz), 8.86 (1H, s)

EXAMPLE 25

A mixture of tetraethyl 2,2'-[2,4-quinazolinediylbis-(iminomethylidyne)]bispropanedioate (2.2 g) in diphenylether (11 ml) was stirred for 35 minutes at 260° C. and then cooled to ambient temperature. To the reaction mixture was added hexane to give crystals, which were separated by filtration and dried to give crude crystals (1.3 g), which were recrystallized from ethanol to give diethyl 4,9-dioxo-4H,9H-pyrimido[1,2-c]pyrimido[1,2-a]-quinazoline-3,8-dicarboxylate (0.9 g).

mp: 193°–195° C.

IR (Nujol) $\nu$max: 1760, 1720, 1680, 1640, 1600 cm$^{-1}$

N.M.R. $\delta$ppm (CDCl$_3$): 1.43 (6H, t, J=8.0 Hz), 4.40 (4H, quartet, J=8.0 Hz), 7.5–8.0 (2H, m), 8.67 (1H, s), 8.67–9.16 (2H, m), 9.73 (1H, s)

EXAMPLE 26

A mixture of 2,2-dimethyl-5-[(4-quinazolinyl)amino]-methylene-1,3-dioxane-4,6-dione (3.5 g) in diphenylether (15 ml) was stirred for 10 minutes at 250°–260° C. and then cooled to ambient temperature. To the reaction mixture was added hexane and allowed to to stand at ambient temperature to give crystals, which were separated by filtration and washed with hexane to give crude crystals (3 g). The crude crystals were subjected to a column chromatography using silica gel (developing solvent: a mixture of ethyl acetate and hexane (3:7)). The eluate was concentrated under reduced pressure to give crystals, which were recrystallized from chloroform and hexane to give 4H-pyrimido[1,2-c]quinazoline-4-one (1.6 g).

mp: 181°14 183° C.

IR (Nujol) $\nu$max: 1700, 1625, 1610, 1582 cm$^{-1}$

N.M.R. $\delta$ppm (CDCl$_3$): 6.57 (1H, d, J=7.0 Hz), 7.86 (3H, m), 8.27 (1H, d, J=7.0 Hz), 8.76 (1H, broad d, J=8.0 Hz), 9.53 (1H, s)

EXAMPLE 27

A mixture of methyl 4-oxo-4H-pyrimido[1,2-c]-quinazoline-3-carboxylate (6.3 g) and lithium iodide (15.8 g) in N,N-dimethylformamide (100 ml) was stirred for 2 hours and a half at 150° C. and then cooled to ambient temperature. To the reaction mixture was added water separated by filtration, washed with water (600 ml) and dried to give crystalline 4-oxo-4H-pyrimido[1,2-c]quinazoline-3-carboxylic acid (0.9 g).

mp: >270° C.

IR (Nujol) $\nu$max: 1720, 1620 cm$^{-1}$

N.M.R. $\delta$ppm (CF$_3$COOH): 8.10–8.66 (3H, m), 8.9–9.2 (1H, m), 9.53 (1H, s), 10.16 (1H, s)

EXAMPLE 28

A mixture of 4-amino-6-(3,3-dimethylbutyramido)-quinazoline (8.5 g), dimethyl methoxymethylenepropanedioate (12.75 g) and N,N-dimethylformamide (34 g) was stirred for an hour at 100° C. After cooling to ambient temperature, to the resultant mixture was added water to give precipitates, which were separated by filtration, washed with water and dried to give crystalline dimethyl [{6-(3,3-dimethylbutyramido)-4-quinazolinylamino}methylene]propanedioate (10.9 g).

mp: 196°–198° C.

IR (Nujol) $\nu$max: 3540, 3350, 3250, 1705, 1680, 1660, 1650, 1610 cm$^{-1}$

N.M.R. $\delta$ppm (CDCl$_3$): 1.10 (9H, s), 2.3 (2H, s), 4.83 (3H, s), 4.9 (3H, s), 7.93 (2H, s), 8.3 (2H, m), 8.8 (1H, s); 9.3 (1H, d, J=12.0 Hz), 11.9 (1H, d, J=12.0 Hz)

EXAMPLE 29

A mixture of 4-amino-6-(3,3-dimethylbutyramido)-quinazoline (12.2 g), diethyl ethoxymethylenepropandioate (15.3 g) and N,N-dimethylformamide (50 ml) was stirred at 150° C. for 2 hours. The reaction mixture was cooled to ambient temperature. After adding water, the resultant mixture was extracted with chloroform. The chloroform layer was washed twice with water and once with saturated aqueous sodium chloride, dried over anhydrous magnesium sulfate and concentrated under reduced pressure to give a residue, to which was added ethyl acetate. Insoluble materials were separated by filtration and dried to give ethyl 4-oxo-10-(3,3-dimethylbutanamido)-4H-pyrimido[1,2-c]quinazoline-3-carboxylate (4.7 g) melting at 253°–254° C. Further, the filtrate was concentrated under reduced pressure to give a residue, which was recrystallized from a mixture of ethyl acetate and hexane to give crystalline diethyl [{6-(3,3-dimethylbutyramido)4-quinazolinylamino}methylene]propanedioate (10.1 g).

mp: 133°–135° C.

IR (Nujol) $\nu$max: 3350, 1695, 1640, 1625, 1610 cm$^{-1}$

N.M.R. $\delta$ppm (CDCl$_3$): 1.15 (9H, s), 1.38 (3H, t, J=6.0 Hz), 1.40 (3H, t, J=6.0 Hz), 2.35 (2H, s), 4.33 (2H, q, J=6.0 Hz), 4.43 (2H, q, J=6.0 Hz), 7.80 (1H, s), 7.9–8.1 (2H, m), 8.20 (1H, s), 8.86 (1H, s), 9.33 (1H, d, J=12.0 Hz), 12.0 (1H, d, J=12.0 Hz)

Anal. calcd. for C$_{22}$H$_{28}$N$_4$O$_5$: C 61.66; H 6.54; N 13.08. Found: C 61.51; H 6.49; N 13.19.

EXAMPLE 30

A mixture of 4-amino-6-pivalamidoquinazoline (2.44 g), dimethyl methoxymethylenepropanedioate (2.61 g) and N,N-dimethyl formamide (10 ml) was stirred at 100° C. for an hour. After cooling to ambient temperature, to the mixture was added water. The mixture was stirred to give crystals, which was filtered off and purified by a column chromatography on silicagel [developing solvent: a mixture of ethyl acetate and chloroform (1:2)] to give crystals (3.48 g), which were dissolved in chloroform. To the solution was added activated charcoal. The mixture was filtered and the filtrate was concentrated under reduced pressure to give crystals, which were recrystallized from ethyl acetate to give crystalline dimethyl [{6-pivalamido—4-quinazolinylamino}methylene]propanedioate (2.3 g).

mp: 189°-190° C.

IR (Nujol) νmax: 3400, 3350, 1750, 1690, 1630, 1615 cm$^{-1}$

N.M.R. δppm (CDCl$_3$): 1.4 (9H, s), 3.8 (3H, s), 3.93 (3H, s), 7.85 (1H, s), 8.00 (2H, m), 8.45 (1H, s), 8.9 (1H, s), 9.4 (1H, d, J=12.0 Hz)

Anal. Calcd. for C$_{19}$H$_{22}$N$_4$O$_5$: C 59.06; H 5.74; N 14.50. Cound: C 58.99; H 5.53; N 14.21.

EXAMPLE 31

A mixture of 4-amino-6-methanesulfonamidoquinazoline (2.0 g), diethyl ethoxymethylenepropanedioate (3.15 g) and N,N-dimethylformamide (16 ml) was stirred at 140° C. for an hour and a half. To the reaction mixture was added diethyl ethoxymethylenepropanedioate (1.57 g). The reaction mixture was stirred for an hour and cooled to ambient temperature. To the mixture was added water to five crystals, which were filtered off and dissolved in a mixture of chloroform and methanol. The solution was dried over anhydrous magnesium sulfate and concentrated under reduced pressure to give a residue, to which was added chloroform. The mixture was heated and insoluble materials were filtered off to give crystalline ethyl 4-oxo-10-methanesulfonamido-4H-pyrimido[1,2-c]quinazoline-3-carboxylate (0.12 g) melting at 310°-312° C. Further, the filtrate was concentrated under reduced pressure and allowed to stand at ambient temperature to give crystals (1.63 g), which were purified by a column chromatography on silica gel (60 g) (developing solvent: 3% methanol-chloroform solution). The crystals were dissolved in 10% methanol-chloroform solution. The solution was treated with activated charcoal and concentrated under reduced pressure. The residue was recrystallized from chloroform to give crystalline diethyl [{6-methanesulfonamido-4-quinazolinylamino}methylene]propanedioate (1.45 g).

mp: 200°-202° C.

IR (Nujol) νmax: 3500, 3210, 1720, 1690, 1675, 1640, 1625, 1600 cm$^{-1}$

N.M.R. δppm (DMSO-d$_6$): 1.3 (3H, t, J=7.0 Hz), 1.35 (3H, t, J=7.0 Hz), 3.16 (3H, s), 4.25 (2H, q, J=7.0 Hz), 4.38 (2H, q, J=7.0 Hz), 7.8-8.1 (3H, m), 8.9 (1H, s), 9.2 (1H, d, J=12.0 Hz), 10.53 (1H, s), 11.55 (1H, d, J=12.0 Hz)

EXAMPLE 32

A mixture of 4-amino-6-methanesulfonamidoquinazoline (6.89 g), diethyl ethoxymethylenepropanediate (15.5 g) and N,N-dimethylformamide (55 ml) was stirred at 155° C. for 2.5 hours. The reaction mixture was cooled to ambient temperature. To the mixture was added water to give precipitates, which were separated by filtration and washed with water. To the crystals was added a mixture of methanol and chloroform (1:4) (400 ml). After stirring under heating, insoluble materials (6.95 g) were filtered off and recrystallized from N,N-dimethylformamide to give crystalline ethyl 4-oxo-10-methanesulfonamido-4H-pyrimido [1,2-c]quinazoline-3-carboxylate (5.76 g).

mp: 310°-312° C.

IR (Nujol) νmax: 3200, 3050, 1725, 1665, 1610 cm$^{-1}$

N.M.R. δppm (DMSO-d$_6$): 1.3 (3H, t, J=7.0 Hz), 3.1 (3H, s), 4.3 (2H, q, J=7.0 Hz), 7.7-8.1 (2H, m), 8.56 (1H, d, J=2.0 Hz), 8.9 (1H, s), 9.4 (1H, s), 10.5 (1H, m)

Anal. Calcd. for C$_{15}$H$_{14}$N$_4$O$_5$S: C 49.72; H 3.89; N 15.46; S 8.85. Found: C 49.88; H 3.96; N 15.52; S 8.71.

EXAMPLE 33

A mixture of 4-amino-6-methanesulfonamidoquinazoline (6.68 g), dimethyl methoxymethylenepropanedioate (6.35 g) and N,N-dimethylformamide (27 ml) was stirred at 100° C. for an hour. The reaction mixture was cooled to ambient temperature. To the mixture was added water to give crystals, which were filtered off and recrystallized from N,N-dimethylformamide to gibe crystalline dimethyl [{6-methanesulfonamido-4-quinazolinylamino}methylene]propanedioate (7.20 g).

mp: 284°-287° C.

IR (Nujol) νmax: 3230, 3130, 1730, 1690, 1650, 1625, 1600 cm$^{-1}$

N.M.R. δppm (DMSO$_4$-d$_6$): 3.12 (3H, s), 3.76 (3H, s), 3.90 (3H, s), 7.7-8.1 (4H, m), 8.86 (1H, s), 9.26 (1H, m)

EXAMPLE 34

(1) A solution of diethyl [(6-nitro-4-quinazolinylamino)methylene]propanedioate (10.8 g) in N,N-dimethylformamide (325 ml) was shaken with 10% palladium on carbon (3.6 g) in hydrogen atmosphere at ambient temperature. After the absorption of hydrogen was finished, the catalyst was removed by filtration. The filtrate was concentrated under reduced pressure to give a residue, to which was added benzene. The mixture was concentrated under reduced pressure to give crude crystals of diethyl [(6-amino-4-quinazolinylamino)methylene]propanedioate.

(2) A mixture of diethyl [(6-amino-4-quinazolinylamino)methylene]propanedioate as obtained above, pyridine (3.32 g) and dry methylene chloride (200 ml) was stirred under ice-cooling. To the mixture was added dropwise a solution of 3,3-dimethylbutyryl chloride (4.8 g) in methylene chloride (10 ml) during 50 minutes under ice-cooling. The reaction mixture was stirred under ice-cooling for 3 hours and 10 minutes. To the mixture was added ice-water. After stirring, the mixture was extracted with methylene chloride. The organic layer was washed with water and saturated aqueous sodium chloride, dried over anhydrous magnesium sulfate and concentrated under reduced pressure to give a residue, which was subjected to a column chromatography on slica gel (200 g) (Developing solvent: methylene chloride) to give fraction A and fraction B. The fraction A was concentrated under reduced pressure to give crystals (4.28 g), which were dissolved in ethyl acetate, treated with activated charcoal and recrystallized to give crystalline diethyl [{6-(3,3-dimethylbutyramido)-4-quinazolinylamino}-methylene]propanedioate (2.29 g).

mp: 133°-135° C.

IR (Nujol) νmax: 3350, 1695, 1640, 1625, 1610 cm$^{-1}$

N.M.R. δppm (CDCl$_3$): 1.15 (9H, s), 1.38 (3H, t, J=6.0 Hz), 1.40 (3H, t, J=6.0 Hz), 2.35 (2H, s), 4.33 (2H, q, J=6.0 Hz), 4.43 (2H, q, J=6.0 Hz), 7.80 (1H, s), 7.9-8.1 (2H, m), 8.2 (1H, s), 8.86 (1H, s), 9.33 (1H, d, J=12.0 Hz), 12.0 (1H, d, J=12.0 Hz)

Anal. Calcd. for C$_{22}$H$_{28}$N$_4$O$_5$: C 61.66; H 7.54; N 13.08. Found: C 61.51; H 6.49; N 13.19.

Further, the fraction B was concentrated under reduced pressure to give crystals (2.6 g), which were dissolved in hexane, treated with activated charcoal and recrystallized to give crystals (1.48 g). A part (1.25 g) of the crystals was purified by a column chromatography on silica gel (20 g) and recrystallized from hexane to give diethyl [[6-{bis(3,3-dimethylbutyryl)amino}-4-quinazolinylamino]methylene]propanedioate (0.9 g).

mp: 100°-102° C.

IR (Nujol) νmax: 3200, 1775, 1730, 1710, 1645, 1625, 1610, 1560 cm$^{-1}$

N.M.R. δppm (CDCl$_3$): 1.03 (9H, s), 1.06 (9H, s), 1.33 (3H, t, J=7.0 Hz), 1.40 (3H, t, J=7.0 Hz), 2.30 (2H, s), 2.45 (2H, s), 4.3 (2H, q, J=7.0 Hz), 4.4 (2H, q, J=7.0 Hz), 7.9-8.15 (3H, m), 9.25 (1H, s), 9.8 (1H, d, J=12.0 Hz)

Anal. Calcd. for $C_{28}H_{38}N_4O_6 \cdot H_2O$: C 61.74; H 7.40; N 10.60. Found: C 61.81; H 7.19; N 10.29.

EXAMPLE 35

A mixture of dimethyl [{6-pivalamido—4-quinazolinylamino}methylene]propanedioate (24.5 g) and diphenyl ether (150 ml) was heated at 260° C. for 20 minutes and cooled to ambient temperature. To the reaction mixture was added hexane to give crystals, which were filtered off, washed with hexane and dissolved in chloroform (400 ml) under heating. Insoluble materials were removed by filtration. The filtrate was concentrated under reduced pressure to 200 ml and allowed to stand under cooling. The precipitated crystals were filtered off and washed with chloroform to give crystalline methyl 4-oxo-10-pivalamido—4H-pyrimido[1,2-c]quinazoline-3-carboxylate (18.29 g). The mother liqour was concentrated under reduced pressure to give crystals, which were purified by a column chromatography on silica gel (50 g) (Developing solvent: 5% methanol-chloroform solution) and recrystallized from chloroform to give the same object compound (3.2 g).

mp: 239°-240° C.

IR (Nujol) νmax: 3380, 1715, 1685, 1610 cm$^{-1}$

N.M.R. δppm (CDCl$_3$): 1.4 (9H, s), 3.96 (3H, s), 7.85 (1H, s), 8.0 (1H, d, J=9.0 Hz), 8.4 (1H, dd, J=3.0 and 9.0 Hz), 8.9 (1H, d, J=3.0 Hz), 9.05 (1H, s), 9.63 (1H, s)

EXAMPLE 36

A mixture of dimethyl [(6-methanesulfonamido-4-quinazolinylamino)methylene]propanedioate (7.2 g) and diphenyl ether (43 ml) was stirred at 250° C. for 15 minutes and then cooled to ambient temperature to give crystals, which were filtered off and washed with a mixture of chloroform and methanol to give crystalline methyl 4-oxo-10-methanesulfonamido-4H-pyrimido[1,2-c]quinazoline-3-carboxylate (4.72 g).

mp: 293°-296° C.

IR (Nujol) νmax: 3220, 1725, 1670, 1608 cm$^{-1}$

EXAMPLE 37

A mixture of diethyl [{6-(3,3-dimethylbutyramido-4-quinazolinylamino}methylene]propandioate (13.1 g) and diphenyl ether (79 ml) was stirred at 250° C. for 15 minutes and cooled to ambient temperature. To the mixture was added hexane. The resultant mixture was stirred to give precipitates, which were separated by filtration and dissolved in a mixture of chloroform and methanol. To the mixture was added charcoal and the mixture was stirred and filtered. The filtrate was concentrated under reduced pressure to give crystals, which were recrystallized from a mixture of chloroform and hexane to give crystalline ethyl 4-oxo-10-(3,3-dimethylbutyramido)-4H-pyrimido[1,2-c]quinazoline-3-carboxylate (9.15 g).

mp: 253°-254° C.

IR (Nujol) νmax: 3350, 1715, 1680, 1615, 1585, 1565, 1505 cm$^{-1}$

N.M.R. δppm (DMSO-d$_6$): 1.1 (9H, s), 1.3 (3H, t, J=8.0 Hz), 2.26 (2H, s), 4.3 (2H, q, J=8.0 Hz), 7.9 (1H, d, J=9.0 Hz), 8.16 (1H, dd, J=2.0 and 9.0 Hz), 8.9 (1H, s), 9.15 (1H, d, J=2.0 Hz), 9.4 (1H, s), 10.36 (1H, s)

Anal. Calcd for $C_{20}H_{22}N_4O_4$: C 62.81; H 5.80; N 14.65. Found: C 62.69; H 5.77; N 14.67.

EXAMPLE 38

A mixture of dimethyl [{6-(3,3-dimethylbutyramido)-4-quinazolinylamino}methylene]propanedioate (7.30 g) and diphenylether (44 ml) was stirred at 260° C. for 10 minutes and then cooled to ambient temperature. To the mixture was added hexane to give crystals, which were filtered off and washed with hexane to give crystalline methyl 4-oxo-10-(3,3-dimethylbutyramido)-4H-pyrimido[1,2-c]quinazoline-3-carboxylate (6.28 g).

mp: 247°-249° C.

IR (Nujol) νmax: 3350, 1740, 1720, 1685, 1610 cm$^{-1}$

N.M.R. δppm (DMSO-d$_6$): 1.1 (9H, s), 2.33 (2H, s), 3.9 (3H, s), 7.96 (1H, d, J=9.0 Hz), 8.23 (1H, dd, J=2.0 and 9.0 Hz), 9.00 (1H, s), 9.22 (1H, s), 9.46 (1H, s), 10.43 (1H, s)

EXAMPLE 39

A mixture of methyl 4-oxo-10-pivalamido—4H-pyrimido[1,2-c]quinazoline-3-carboxylate (1.27 g), anhydrous lithium iodide (3.18 g) and dry pyridine (13 ml) was stirred at 120° C. for 3 hours and then concentrated under reduced pressure to give a residue, which was dissolved in water. Insoluble materials were removed by filtration. The filtrate was adjusted to pH 1 with conc. hydrochloric acid to give crystals, which were filtered off and washed with water. To the crude crystals was added methanol. The mixture was stirred and filtered to give crystals (1.0 g), which were washed with a mixture of chloroform and methanol to give crystalline 4-oxo-10-pivalamido—4H-pyrimido[1,2-c]quinazoline-3-carboxylic acid (0.65 g).

mp: 330°-332° C.

IR (Nujol) νmax: 3340, 1720, 1680, 1660, 1610 cm$^{-1}$

N.M.R. δppm (DMSO-d$_6$): 1.25 (9H, s), 7.9 (1H, d, J=9.0 Hz), 8.35 (1H, dd, J=2.0 and 9.0 Hz), 8.93 (1H, s), 9.13 (1H, d, J=2.0 Hz), 9.4 (1H, s), 9.75 (1H, s)

Anal. Calcd. for $C_{17}H_{16}N_4O_4$: C 59.99; H 4.74; N 16.46. Found: C 59.49; H 4.60; N 16.39.

EXAMPLE 40

A mixture of methyl 4-oxo-10-methanesulfonamido-4H-pyrimido[1,2-c]quinazoline-3-carboxylate (4.32 g), anhydrous lithium iodide (10.8 g) and dry pyridine (43 ml) was stirred at 120° C. for 2 hours. The reaction mixture was concentrated under reduced pressure to give a residue, which was dissolved in water (900 ml). Insoluble materials were removed by filtration. The aqueous layer was adjusted to pH 5 with conc. hydrochloric acid to give crystals, which were filtered off, suspended in a mixture of chloroform and methanol, stirred and filtered to give crystals, which were dried to give crystalline 4-oxo-10-methanesulfonamido-4H-pyrimido[1,2-c]quinazoline-3-carboxylic acid (2.8 g).

mp: 319°-322° C.

IR (Nujol) νmax: 3350, 3450, 1695, 1680, 1605 cm$^{-1}$

N.M.R δppm (DMSO-d$_6$): 3.20 (3H, s), 7.8-8.2 (2H, m), 8.65 (1H, d, J=2.0 Hz), 9.0 (1H, s), 9.5 (1H, s), 10.56 (1H, s)

EXAMPLE 41

A mixture of methyl 4-oxo-10-(3,3-dimethylbutyramido)-4H-pyrimido[1,2-c]quinazoline-3-carboxylate (6.0 g), anhydrous lithium iodide (15.0 g) and dry pyridine (60 ml) was stirred at 120° C. for 2 hours. The reaction mixture was concentrated under reduced pressure to give a residue, to which was added water. The mixture was filtered to give crystals, which were suspended in water (100 ml) and adjusted to pH 1-2 with con. hydrochloric acid to give crystals, which were separated by filtration and dried to give crystalline 4-oxo-10-(3,3-dimethylbutyramido)-4H-pyrimido[1,2-c]quinazoline-3-carboxylic acid (2.5 g).

mp: 304°–306° C.

IR (Nujol) $\nu$max: 3330, 1730, 1690, 1660, 1610 cm$^{-1}$

N.M.R. $\delta$ppm (DMSO-d$_6$): 1.00 (9H, s), 2.26 (2H, s), 7.93 (1H, d, J=9.0 Hz), 8.16 (1H, dd, J=2.0 and 9.0 Hz), 8.96 (1H, s), 9.20 (1H, d, J=2.0 Hz), 9.43 (1H, s), 10.40 (1H, s)

EXAMPLE 42

A mixture of 4-amino-6-(2-ethylbutyramido)quinazoline (5.58 g), dimethyl methoxymethylenepropanedioate (5.62 g) and N,N-dimethylformamide (22 ml) was stirred at 100° C. for 1.5 hours. After cooling to ambient temperature, water (90 ml) was added to the reaction mixture. The resulting solid was separated by filtration, washed with water and dried to give dimethyl [[6-(2-ethylbutyramido)-4-quinazolinylamino]methylene]propanedioate (4.85 g).

m.p. 221°–225° C.

IR (Nujol), $\nu$max: 3280, 1725, 1660, 1630, 1610, 1570, 1525 cm$^{-1}$

N.M.R. $\delta$ppm (DMSO-d$_6$): 0.92 (6H, t, J=7.0 Hz), 1.3–1.8 (4H, m), 2.0–2.5 (1H, m), 3.76 (3H, s), 3.92 (3H, s), 7.9 (1H, d, J=10.0 Hz), 8.2 (1H, dd, J=2.0, 10.0 Hz), 8.56 (1H, d, J=2.0 Hz), 8.83 (1H, s), 9.23 (1H, d, J=12.0 Hz), 10.5 (1H, s), 11.52 (1H, d, J=12.0 Hz)

EXAMPLE 43

A mixture of 4-amino-6-(2-methylpropionamido)-quinazoline (6.2 g) and dimethyl methoxymethylenepropanedioate (7.01 g) in N,N-dimethylformamide (25 ml) was stirred at 100° C. for 1.5 hours and cooled to room temperature. Water was added to the reaction mixture. The resulting solid was separated by filtration, washed with water and dried to give dimethyl [[6-(2-methylpropionamido)-4-quinazolinylamino]methylene]propanedioate (8.9 g). Recrystallization from ethyl acetate gave pure crystals melting at 212°–214° C.

IR (Nujol), $\nu$max: 3270, 1710, 1660, 1630, 1610, 1560, 1530 cm$^{-1}$

N.M.R. $\delta$ppm (DMSO-d$_6$): 1.20 (6H, d, J=7.0 Hz), 2.40–2.66 (1H, m), 3.76 (3H, s), 3.90 (3H, s), 7.93 (1H, d, J=9.0 Hz), 8.08 (1H, d, J=9.0 Hz), 8.4 (1H, s), 8.73 (1H, s), 9.13 (1H, d, J=12.0 Hz), 10.4 (1H, s), 11.13 (1H, d, J=12.0 Hz), Anal. Calcd. for C$_{18}$H$_{20}$N$_4$O$_5$: C, 58.06; H, 5.41; N, 15.03. Found: C, 58.14; H, 5.39; N, 15.19.

EXAMPLE 44

A mixture of 4-amino-6-cyclohexanecarboxamidoquinazoline (8.85 g) and dimethyl methoxymethylenepropanedioate (8.55 g) in N,N-dimethylformamide (35 ml) was stirred at 100° C. for 1 hour. After cooling to ambient temperature, water was added to the reaction mixture. The resulting solid was collected by filtration, washed with water and dried. The solid was chromatographed on silica gel with 1% methanol-chloroform and recrystallized from chloroform to give a crystalline solid (6.13 g). The solid is a mixture of dimethyl [[6-cyclohexanecarboxamido-4-quinazolinylamino]methylene]propanedioate and methyl 4-oxo-10-cyclohexanecarboxamido-4H-pyrimido[1,2-C]quinazoline-3-carboxylate in the ratio of about 2:1.

mp. 210°–212° C.

IR (Nujol) $\nu$max: 3330, 1735, 1710, 1682, 1662, 1625, 1608 cm$^{-1}$

EXAMPLE 45

A mixture of 4-amino-6-(3-cyclopentylpropionamido)quinazoline (7.05 g) and dimethyl methoxymethylenepropanedioate (6.48 g) in N,N-dimethylformamide (28 ml) was stirred at 100° C. for 1 hour and 10 minutes. After cooling to ambient temperature, water was added to the reaction mixture. The resulting solid was separated by filtration, washed with water, and dried. The crude crystals were dissolved in a mixture of chloroform and methanol, treated with activated charcoal, and evaporated under reduced pressure until crystallization began. After cooling, the resulting solid was collected, washed with methanol and with dichloromethane, and dried. There was obtained crystalline methyl 4-oxo-10-(3-cyclopentylpropionamido)-4H-pyrimido[1,2-C]quinazoline-3-carboxylate (2.16 g). The filtrate was evaporated under reduced pressure to give a residue which was chromatographed on silica gel with 1% methanoldichloromethane. The first fractions contained methyl 4-oxo-10-(3-cyclopentylpropionamido)-4H-pyrimido[1,2-C]quinazoline-3-carboxylate (1.9 g). The second fractions contained dimethyl [[6-(3-cyclopentylpropionamido)-4-quinazolinylamino]methylene]propanedioate (5.16 g).

mp. 193°–197° C.

IR (Nujol) $\nu$max: 3340, 1745, 1708, 1690, 1660, 1630, 1620 cm$^{-1}$

N.M.R. $\delta$ppm (DMSO-d$_6$): 0.8–2.1 (11H, m), 2.23 (2H, t, J=7.0 Hz), 3.75 (3H, s), 3.90 (3H, s), 7.78 (1H, d, J=9.0 Hz), 8.05 (1H, d, J=9.0 Hz), 8.36 (1H, s), 8.73 (1H, s), 9.11 (1H, d, J=12.0 Hz), 10.40 (1H, s), 11.40 (1H, d, J=12.0 Hz)

EXAMPLE 46

A mixture of dimethyl[[6-(2-ethylbutyramido)-4-quinazolinylamino]methylene]propanedioate (5.3 g) and diphenyl ether (32 ml) was heated at 255° C. for 15 minutes and cooled to ambient temperature. Hexane was added to the reaction mixture. The resulting crystals were filtered off, washed with hexane and dried. The crude crystals were dissolved in a mixture of chloroform and methanol (10:1) under heating. Insoluble materials were removed by filtration. The filtrate was concentrated under reduced pressure to give crystals, which were recrystallized from a mixture of chloroform and hexane to give methyl 4-oxo-10-(2-ethylbutyramido)-4H-pyrimido[1,2-C]quinazoline-3-carboxylate (3.81 g).

mp. 239°–240° C.

IR (Nujol) $\nu$max: 3350, 1730, 1690, 1665, 1610, 1490 cm$^{-1}$

N.M.R. $\delta$ppm (DMSO-d$_6$): 0.92 (6H, t, J=8.0 Hz), 1.24–1.84 (4H, m), 2.12–2.42 (1H, m), 3.84 (3H, s), 7.92 (1H, d, J=8.0 Hz), 8.18 (1H, dd, J=2.0, 8.0 Hz), 8.88 (1H, s), 9.12 (1H, d, J=2.0 Hz), 9.38 (1H, s), 10.4 (1H, s)

Anal. Calcd. for C$_{19}$H$_{20}$N$_4$O$_4$: C, 61.94; H, 5.47; N, 15.21. Found: C, 61.71; H, 5.55; N, 15.38.

EXAMPLE 47

A mixture of dimethyl [[6-(2-methylpropionamido)-4-quinazolinylamino]methylene]propanedioate (8.4 g) in diphenyl ether (42 ml) was stirred at 255° C. for 15 minutes. The reaction mixture was cooled to ambient temperature to give crystals which were filtered off, washed with hexane and dried. There were obtained 6.9 g of the crude crystals. The crude crystals were dissolved in a mixture of chloroform and methanol (4:1) under heating. Insoluble materials were removed by filtration. The filtrate was concentrated under reduce pressure to about 150 ml. After cooling, there was obtained crystalline methyl 4-oxo-10-(2-methyl-propionamido)-4H-pyrimido[1,2-C]quinazoline-3-carboxylate (5.85 g).

mp. 275°–277° C.

IR (Nujol) νmax: 3345, 1700, 1670, 1610, 1580, 1560 cm$^{-1}$

N.M.R. δppm (DMSO-d$_6$): 1.16 (6H, d, J=7 Hz), 2.4–2.8 (1H, m), 3.86 (3H, s), 7.93 (1H, d, J=9 Hz), 8.22 (1H, dd, J=2, 9 Hz), 8.93 (1H, s), 9.2 (1H, d, J=2 Hz), 9.43 (1H, s), 10.43 (1H, s)

Anal. Calcd. for C$_{17}$H$_{16}$N$_4$O$_4$: C, 59.99; H, 4.74; N, 16.46. Found: C, 59.73; H, 4.58; N, 16.37.

EXAMPLE 48

A mixture of dimethyl [[6-cyclohexanecarboxamido-4-quinazolinylamino]methylene]propanedioate (4 g) and diphenyl ether (31 ml) was stirred at 260° C. for 15 minutes. After cooling to ambient temperature, the resulting solid was collected by filtration, washed with hexane and dried. There was obtained methyl 4-oxo-10-cyclohexanecarboxamido-4H-pyrimido[1,2-C]quinazoline-3-carboxylate (3.6 g).

mp. 250°–251° C.

N.M.R. δppm (DMSO-d$_6$): 1.1–2.1 (10H, m), 2.2–2.8 (1H, m), 3.86 (3H, s), 7.9 (1H, d, J=9.0 Hz), 8.18 (1H, dd, J=2.0, 9.0 Hz), 8.9 (1H, s), 9.13 (1H, d, J=2.0 Hz), 9.4 (1H, s), 10.36 (1H, s)

Anal. Calcd. for C$_{20}$H$_{20}$N$_4$O$_4$: C, 63.15; H, 5.30; N, 14.73. Found: C, 63.12; H, 5.24; N, 14.78.

EXAMPLE 49

A mixture of dimethyl [[6-(3-cyclopentylpropionamido)-4-quinazolinylamino]methylene]propanedioate (6.9 g) in diphenyl ether (53 ml) was stirred at 255° C. for 15 minutes and cooled to ambient temperature. The resulting solid was collected, washed with hexane and dried. There was obtained methyl 4-oxo-10-(3-cyclopentylpropionamido)-4H-pyrimido[1,2-C]quinazoline-3-carboxylate (4.5 g).

mp. 244°–247° C.

IR (Nujol) νmax: 3350, 1712, 1682, 1612 cm$^{-1}$

N.M.R. δppm (DMSO-d$_6$): 1.0–2.0 (11H, m), 2.3 (2H, m), 3.85 (3H, s), 7.8–8.2 (2H, m), 8.93 (1H, s), 9.20 (1H, s), 9.43 (1H, s), 10.50 (1H, s)

EXAMPLE 50

A mixture of methyl 4-oxo-10-(2-ethylbutyramido)-4H-pyrimido[1,2-C]quinazoline-3-carboxylate (3.2 g), anhydrous lithium iodide (8.0 g) and dry pyridine (32 ml) was stirred at 120° C. for 1.5 hours. The reaction mixture was concentrated under reduced pressure to give a residue, which was dissolved in water. Insoluble materials were removed by filtration. The aqueous layer was adjusted to pH 1-2 with conc. hydrochloric acid to give crystals, which were separated by filtration and dried. The crude crystals were washed with methanol three times and recrystallized from acetonitrile to give 4-oxo-10-(2-ethylbutyramido)-4H-pyrimido[1,2-C]quinazoline-3-carboxylic acid (0.7 g).

mp. 295°–298° C.

N.M.R. δppm (DMSO-d$_6$): 0.96 (6H, t, J=7.0 Hz), 1.3–1.9 (4H, m), 2.0–2.6 (1H, m), 8.0 (1H, d, J=9.0 Hz), 8.26 (1H, dd, J=2.0, 9.0 Hz), 9.0 (1H, s), 9.26 (1H, d, J=2.0 Hz), 9.5 (1H, s), 10.5 (1H, s)

EXAMPLE 51

A mixture of methyl 4-oxo-10-(2-methylpropionamido)-4H-pyrimido[1,2-C]quinazoline-3-carboxylate (5.42 g) and anhydrous lithium iodide (13.55 g) in dry pyridine (54 ml) was stirred at 100° C. for 1.5 hours. The reaction mixture was cooled to give crytals which were collected by filtration and washed with pyridine. The crystals were suspended in water (200 ml). The suspension was adjusted to pH 2.5–3.0 with conc. hydrochloric acid to give yellow crystals, which were separated by filtration, washed with water and dried. The crude crystals were washed with a mixture of chloroform and methanol (1:1) two times and dried. There was obtained crystalline 4-oxo-10-(2-methylpropionamido)-4H-pyrimido[1,2-C]quinazoline-3-carboxylic acid (3.80 g).

mp. 312°–314° C.

IR (Nujol) νmax: 3350, 1730, 1698, 1655, 1620 cm$^{-1}$

N.M.R. δppm (DMSO-d$_6$): 1.15 (6H, d, J=7.0 Hz), 2.4–2.8 (1H, m), 7.9 (1H, d, J=9.0 Hz), 8.2 (1H, dd, J=2.0, 9.0 Hz), 8.93 (1H, s), 9.15 (1H, d, J=2.0 Hz), 9.36 (1H, s), 10.4 (1H, s)

Anal. Calcd. for C$_{16}$H$_{14}$N$_4$O$_4$: C, 58.89; H, 4.32 N, 17.17. Found: C, 58.73; H, 4.36 N, 17.22.

EXAMPLE 52

A mixture of methyl 4-oxo-10-cyclohexanecarboxamido-4H-pyrimido[1,2-C]quinazoline-3-carboxylate (4.7 g) and anhydrous lithium iodide (11.75 g) in dry pyridine (47 ml) was stirred at 100° C. for 1 hour and 20 minutes and cooled to ambient temperature. The resulting solid was collected by filtration and washed with ethanol. The solid was suspended in water (100 ml). The suspension was adjusted to pH 1-2 with conc. hydrochloric acid to give yellow crystals which were separated by filtration, washed with water and dried. The crude crystals were washed with a mixture of chloroform and methanol and dried. There was obtained 4-oxo-10-cyclohexanecarboxamido-4H-pyrimido[1,2-C]quinazoline-3-carboxylic acid (2.75 g).

mp. 311°–314° C.

IR (Nujol) νmax: 3330, 3020, 1740, 1710, 1660, 1610, 1580 cm$^{-1}$

N.M.R. δppm (DMSO-d$_6$): 1.0–2.2 (10H, m), 2.23–2.8 (1H, m), 7.93 (1H, d, J=9.0 Hz), 8.2 (1H, dd, J=9.0, 2.0 Hz), 8.96 (1H, s), 9.2 (1H, d, J=2.0 Hz), 9.45 (1H, s), 10.4 (1H, s)

Anal. Calcd. for C$_{19}$H$_{18}$N$_4$O$_4$: C, 62.28; H, 4.95; N, 15.29; Found: C, 61.59; H, 4.91; N, 15.20

EXAMPLE 53

A mixture of methyl 4-oxo-10-(3-cyclopentylpropionamido)-4H-pyrimido[1,2-C]quinazoline-3-carboxylate (5.72 g) and anhydrous lithium iodide (14.3 g) in dry pyridine (59 ml) was stirred at 120° C. for 1.5 hours. The reaction mixture was concentrated under reduced pressure to give crystalline residue, which was suspended in water (100 ml). The suspension was adjusted to pH 1.7 with conc. hydrochloric acid to yield yellow crystals, which were separated by filtration, washed with water and dried. Recrystallization from N,N-dimethylformamide gave crystalline 4-oxo-10-(3-cyclopentylpropionamido)-4H-pyrimido[1,2-C]quinazoline-3-carboxylic acid (4.4 g).

mp. 279°–283° C.

IR (Nujol) $\nu$max: 3350, 1730, 1690, 1668, 1610, 1600, 1580 cm$^{-1}$

N.M.R. $\delta$ppm (DMSO-d$_6$): 0.7–2.1 (11H, m), 2.4 (2H, m), 7.90 (2H, d, J=8 Hz), 8.16 (1H, dd, J=8.0, 2.0 Hz), 8.93 (1H, s), 9.13 (1H, d, J=2.0 Hz), 9.23 (1H, s), 10.41 (1H, s)

EXAMPLE 54

A mixture of 4-amino-6-(2-ethylbutyramido)quinazoline (0.9 g) and diethyl ethoxymethylenepropanedioate (0.95 g) in N,N-dimethylformamide (4 ml) was stirred at 100° C. for 2 hours and 40 minutes. Water was added to the reaction mixture. The resulting crystals were collected, washed with water and dried. The crude crystals were chromatographed on silica gel with 20% ethyl acetate-chloroform and recrystallized from a mixture of ethyl acetate, chloroform and hexane to give crystalline diethyl [[6-(2-ethylbutyramido)-4-quinazolinylamino]methylene]propanedioate (1.1 g).

mp: 191°–194° C.

IR (Nujol) $\nu$max: 3280, 1720, 1658, 1628, 1610, 1570 cm$^{-1}$

NMR $\delta$ppm (DMSO-d$_6$): 0.92 (6H, t, J=7 Hz), 1.28 (3H, t, J=7 Hz), 1.32 (3H, t, J=7 Hz), 1.56 (4H, m), 2.36 (1H, m), 4.2 (2H, q, J=7 Hz), 4.36 (2H, q, J=7 Hz), 7.88 (1H, d, J=9 Hz), 8.16 (1H, d, J=9 Hz), 8.48 (1H, s), 8.8 (1H, s), 9.16 (1H, d, J=12 Hz), 10.44 (1H, s), 11.4 (1H, d, J=12 Hz)

EXAMPLE 55

A mixture of diethyl [[6-(2-ethylbutyramido)-4-quinazolinylamino]methylene]propanedioate (0.6 g) in diphenyl ether (3 ml) was stirred at 250° C. for 15 minutes and cooled to ambient temperature. The resulting crystals were filtered, washed with ethyl acetate and dried. There was obtained ethyl 4-oxo-10-(2-ethylbutyramido)-4H-pyrimido[1,2-C]quinazoline-3-carboxylate (0.5 g).

mp 220°–222° C.

IR (Nujol) $\nu$max: 3340, 1715, 1700, 1668 cm$^{-1}$

NMR $\delta$ppm (DMSO-d$_6$): 0.88 (6H, t, J=7 Hz), 1.32 (3H, t, J=7 Hz), 1.56 (4H, m), 2.35 (1H, m), 4.3 (2H, q, J=7 Hz), 7.92 (1H, d, J=9 Hz), 8.16 (1H, d, J=9 Hz), 8.88 (1H, s), 9.16 (1H, broad d), 9.38 (1H, s), 10.4 (1H, s)

EXAMPLE 56

A mixture of 4-amino-6-(3-cyclopentylpropionamido)quinazoline (4.4 g) and diethyl ethoxymethylenepropanedioate (5.5 g) in N,N-dimethylformamide (20 ml) was stirred at 100° C. for 3 hours. To the reaction mixture was added water. The resulting crystals were collected by filtration, washed with water, and suspended in dichloromethane under heating. After the suspension was cooled to ambient temperature, the resulting crystals were collected by filtration and washed with dichloromethane. There was obtained ethyl 4-oxo-10-(3-cyclopentylpropionamido)-4H-pyrimido[1,2-C]quinazoline-3-carboxylate (2.4 g). The filtrate was concentrated to ¼ of its original volume and cooled to 0° C. to yield an additional 0.37 g of the same product. The cryde substance (2.77 g) obtained above was chromatographed on silica gel with 2% methanol-dichloromethane. The product was recrystallized from a mixture of methanol and dichloromethane to give crystalline pure product (2.45 g).

mp: 241°–246° C.

IR (Nujol) $\nu$max: 3350, 1725, 1685, 1672, 1615, 1582, 1560 cm$^{-1}$

The mother liquor was chromatographed on silica gel with 1.5% methanol-chloroform to give an oil (1.15 g), which was crystallized from a mixture of ethyl acetate and hexane. There was obtained diethyl [[6-(3-cyclopentylpropionamido)-4-quinazolinylamino]methylene]propanedioate (0.82 g).

mp: 155°–158° C.

IR (Nujol) $\nu$max: 3280, 1730, 1660, 1615, 1608, 1568, 1540 cm$^{-1}$

NMR $\delta$ppm (DMSO-d$_6$): 1.30 (3H, t, J=7 Hz), 1.32 (3H, t, J=7 Hz), 0.9–2.0 (11H, m), 2.36 (2H, m), 4.20 (2H, q, J=7 Hz), 4.33 (2H, q, J=7 Hz), 7.80 (1H, d, J=9 Hz), 8.06 (1H, d, J=9 Hz), 8.36 (1H, br s), 8.73 (1H, s), 9.10 (1H, d, J=12 Hz), 10.36 (1H, s), 11.5 (1H, d, J=12 Hz)

EXAMPLE 57

A mixture of 4-amino-6-(2,3-dimethylpentanamido)quinazoline (6.75 g) and dimethyl methoxymethylenepropanedioate (6.48 g) in N,N-dimethylformamide (20 ml) was stirred at 100° C. for 1 hour and cooled to ambient temperature. Water was added to the reaction mixture. The resulting solid was separated by filtration, washed with water, and dried. There was obtained dimethyl [[6-(2,3-dimethylpentanamido)-4-quinazolinylamino]methylene]propanedioate (6.58 g). A portion of the crude product was chromatographed on silica gel with chloroform and ethyl acetate (3:1) and recrystallized from ethyl acetate to give analytically pure dimethyl [[6-(2,3-dimethylpentanamido)-4-quinazolinylamino]methylene]propanedioate (0.45 g).

mp: 216°–217° C.

IR (Nujol) $\nu$max: 3270, 1725, 1660, 1630, 1610, 1565, 1540, 1500 cm$^{-1}$

NMR $\delta$ppm (DMSO-d$_6$): 0.7–2.0 (12H, m), 2.2–2.8 (1H, m), 3.8 (3H, s), 3.93 (3H, s), 7.93 (1H, d, J=9 Hz), 8.2 (1H, dd, J=2,9 Hz), 8.55 (1H, d, J=2 Hz), 8.85 (1H, s), 9.23 (1H, d, J=12 Hz), 10.43 (1H, s), 11.6 (1H, d, J=12 Hz), Anal. Calcd for C$_{21}$H$_{26}$N$_4$O$_5$: C, 60.85; H, 6.32; N, 13.52. Found: C, 61.16; H, 6.15; N, 13.56.

EXAMPLE 58

A mixture of dimethyl [[6-(2,3-dimethylpentanamido)-4-quinazolinylamino]methylene]propanedioate (5.75 g) in diphenyl ether (28 ml) was stirred at 255° C. for 15 minutes and cooled to ambient temperature. The resulting solid was collected by filtration, washed with hexane, and dried. The crude crystals were chromatographed on silica gel with 4% methanol-chloroform. The product was recrystallized from a mixture of methanol and chloroform. There was obtained methyl 4-oxo-10-(2,3-dimethylpentanamido)-4H-pyrimido[1,2-C]quinazoline-3-carboxylate (0.4 g). Concentration of the mother liquor gave a crystalline residue, which was recrystallized from a mixture of chloroform and hexane to give additional 4.25 g of the same product.

mp: 220°–221° C.

IR (Nujol) νmax: 3350, 1715, 1690, 1620, 1585, 1565, 1510 cm$^{-1}$

NMR δppm (DMSO-d$_6$): 0.7-2.0 (12H, m), 2.2-2.7 (1H, m), 3.83 (3H, s), 7.9 (1H, d, J=9 Hz), 8.2 (1H, dd, J=2, 9 Hz), 8.9 (1H, s), 9.33 (1H, d, J=2 Hz), 9.4 (1H, s), 10.36 (1H, s)

Anal. Calcd. for C$_{20}$H$_{22}$N$_4$O$_4$: C, 62.81; H, 5.80; N, 14.65. Found: C, 62.80; H, 5.55; N, 14.66.

EXAMPLE 59

A mixture of methyl 4-oxo-10-(2,3-dimethylpentanamido)-4H-pyrimido[1,2-C]quinazoline-3-carboxylate (3.4 g) and anhydrous lithium iodide (8.5 g) in dry pyridine (34 ml) was stirred at 100° C. for 1 hour and 20 minutes. The reaction mixture was concentrated under reduced pressure. Water was added to the residue to give precipitates, which were collected by filtration and washed with water. The resulting crystals were suspended in water. The suspension was adjusted to pH 1-2 with conc. hydrochloric acid to give yellow crystals, which were separated by filtration, washed with water, and dried. The crude crystals (3.85 g) were dissolved in a mixture of chloroform and methanol under heating. The solution was filtered to remove insoluble materials. The filtrate was concentrated under reduced pressure to 40 ml and cooled in an ice bath. The resulting crystals were collected by filtration and suspended in a mixture of chloroform and methanol under heating. After the suspension was cooled to ambient temperature, the crystals were filtered and dried. There was obtained 4-oxo-10-(2,3-dimethylpentanamido)-4H-pyrimido[1,2-C]quinazoline-3-carboxylic acid (1.0 g).

mp: 286°-288° C.

IR (Nujol) νmax: 3330, 1740, 1700, 1660, 1610, 1580, 1520 cm$^{-1}$

NMR δppm (DMSO-d$_6$): 0.7-1.9 (12H, m), 2.2-2.7 (1H, m), 7.9 (1H, d, J=9 Hz), 8.18 (1H, dd, J=2, 9 Hz), 8.93 (1H, s), 9.16 (1H, d, J=2 Hz), 9.4 (1H, s), 10.33 (1H, s), 12.3-13.1 (1H, broad S)

EXAMPLE 60

A mixture of 4-amino-7-pivalamidoquinazoline (10.5 g) and dimethyl methoxymethylenepropanedioate (10.9 g) in N,N-dimethylformamide (32 ml) was stirred at 100° C. for 1 hour and 25 minutes. After the reaction mixture was cooled to ambient temperature, water was added. The resulting solid was separated by filtration, washed with water and dried. The crystals were recrystallized from a mixture of ethyl acetate and ethanol to give crystalline dimethyl [[7-pivalamido-4-quinazolinylamino]methylene]propanedioate (13.7 g).

mp: 183°-184° C.

IR (Nujol) νmax: 3470, 3250, 1705, 1680, 1650, 1620, 1540 cm$^{-1}$

NMR δppm (DMSO-d$_6$): 1.32 (9H, s), 3.72 (3H, s), 3.82 (3H, s), 7.72 (1H, d, J=10 Hz), 7.92 (1H, dd, J=2, 10 Hz), 7.35 (1H, d, J=2 Hz), 8.72 (1H, s), 9.02 (1H, d, J=12 Hz), 9.66 (1H, s), 11.36 (1H, d, J=12 Hz)

EXAMPLE 61

A mixture of dimethyl [[7-pivalamido-4-quinazolinylamino]methylene]propanedioate (11.7 g) in diphenyl ether (58 ml) was stirred at 250° C. for 15 minutes and cooled to ambient temperature. Hexane was added to the reaction mixture. The resulting crystals were collected by filtration, washed with hexane, and dried. The crystals were dissolved in a mixture of chloroform and ethanol under heating. The solution was filtered to remove insoluble materials. The filtrate was concentrated under reduced pressure until crystallization began. After the solution was cooled to ambient temperature, the resulting crystals were collected by filtration to give methyl 4-oxo-9-pivalamido-4H-pirimido[1,2-C]quinazoline-3-carboxylate (5.1 g). Concentration of the mother liquor gave additional crystals of the same compound (3.4 g).

mp: 260°-262° C.

IR (Nujol) νmax: 3340, 1725, 1680, 1610, 1580, 1560, 1525 cm$^{-1}$

NMR δppm (DMSO-d$_6$): 1.3 (9H, s), 3.8 (3H, s), 8.06 (1H, d, J=9 Hz), 8.36 (1H, s), 8.64 (1H, d, J=9 Hz), 8.84 (1H, s), 9.42 (1H, s), 9.80 (1H, s)

EXAMPLE 62

A mixture of methyl 4-oxo-9-pivalamido-4H-pyrimido[1,2-C]quinazoline-3-carboxylate (6.5 g) and anhydrous lithium iodide (16.25 g) in dry pyridine (65 ml) was stirred at 100° C. for 1 hour and 30 minutes and at 120° C. for additional 30 minutes. The reaction mixture was concentrated under reduced pressure to give an oily residue, which was dissolved in water. The resulting solution was adjusted to pH 1 with conc. hydrochloric acid to give yellow crystals, which were separated by filtration, washed with water, and dried. The crude crystals were dissolved in a mixture of chloroform and methanol under heating. The solution was filtered to remove insoluble materials. The solution was concentrated under reduced pressure until crystallization began and cooled. The resulting crystals were collected by filtration and dried. There was obtained 4-oxo-9-pivalamido-4H-pyrimido-[1,2-C]quinazoline-3-carboxylic acid (2.9 g).

mp: 252°-256° C.

IR (Nujol) νmax: 3370, 3250, 1735, 1690, 1650, 1615, 1550 cm$^{-1}$

NMR δppm (DMSO-d$_6$): 1.30 (9H, s), 8.08 (1H, dd, J=2, 9 Hz), 8.38 (1H, d, J=2 Hz), 8.64 (1H, d, J=9 Hz), 8.86 (1H, s), 9.44 (1H, s), 9.82 (1H, s)

We claim:

1. A pyrimidoquinazoline compound of the formula:

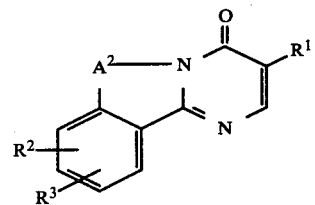

wherein A$^2$ is a group of the formula:

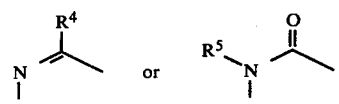

R$^1$ is hydrogen, carboxy or C$_2$-C$_7$ alkoxycarbonyl,

R$^2$ and R$^3$ are hydrogen, C$_1$-C$_6$ alkyl, halogen, nitro amino, C$_1$-C$_6$ alkoxy, phenyloxy, C$_1$-C$_6$ alkylthio, C$_1$-C$_6$ alkylpiperazinyl, C$_1$-C$_{18}$ alkanoylamino, di(C$_1$-C$_6$)alkanoylamino, C$_3$-C$_9$ alkoxalylamino, C$_4$-C$_8$ cycloalkanecarbonylamino, C$_3$-C$_7$ cycloalkyl(C$_1$-C$_6$)alkanoylamino, benzamido, phenyl(-C$_1$-C$_6$)alkanoylamino, C$_1$-C$_6$ alkanesulfonylamino or di($C_1$-$C_6$)alkylamino which may be substituted with hydroxy, $R^4$ is hydrogen, $C_1$-$C_6$ alkyl, hydroxy, $C_1$-$C_6$ alkoxy, $C_2$-$C_6$ alkenyloxy or di($C_1$-$C_6$)alkylamino, and $R^5$ is $C_1$-$C_6$ alkyl or $C_2$-$C_6$ alkenyl, or pharmaceutically acceptable salt thereof.

2. A compound according to claim 1, which is a compound of the formula:

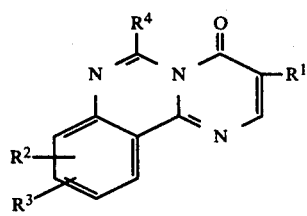

3. A compound according to claim 2, which is methyl 4-oxo-10-pivalamido-4H-pyrimido[1,2-c]quinazoline-3-carboxylate.

4. A compound according to claim 2, which is 4-oxo-10-pivalamido-4H-pyrimido[1,2-c]quinazoline-3-carboxylic acid or pharmaceutically acceptable salt thereof.

5. A compound according to claim 2, which is 4-oxo-10-(3,3-dimethylbutyramido)-4H-pyrimido[1,2-c]quinazoline-3-carboxylic acid or pharmaceutically acceptable salt thereof.

6. A compound according to claim 2, which is 4-oxo-10-(2-methylpropionamido)-4H-pyrimido[1,2-c]quinazoline-3-carboxylic acid or pharmaceutically acceptable salt thereof.

7. A compound according to claim 2, which is 4-oxo-10-(2-ethylbutyramido)-4H-pyrimido[1,2-c]quinazoline-3-carboxylic acid or pharmaceutically acceptable salt thereof.

8. A compound according to claim 2, which is 4-oxo-10-(2,3-dimethylpentanamido)-4H-pyrimido[1,2-c]quinazoline-3-carboxylic acid or pharmaceutically acceptable salt thereof.

9. A compound according to claim 1, which is a compound of the formula:

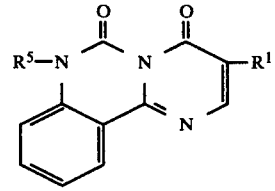

10. An anti-allergic pharmaceutical composition comprising a effective amount of the compound of claim 1 in association with a non-toxic, pharmaceutically acceptable carrier or excipient.

* * * * *